US012735409B2

(12) United States Patent
El Marrouni et al.

(10) Patent No.: US 12,735,409 B2
(45) Date of Patent: Sep. 15, 2026

(54) BENZOXAZINONE DERIVATIVES AS SELECTIVE CYTOTOXIC AGENTS

(71) Applicant: Merck Sharp & Dohme LLC, Rahway, NJ (US)

(72) Inventors: Abdellatif El Marrouni, Ambler, PA (US); Antonella Converso, Elkins Park, PA (US); Ashley Forster, Gilbertsville, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 363 days.

(21) Appl. No.: 18/698,450

(22) PCT Filed: Oct. 10, 2022

(86) PCT No.: PCT/US2022/046143

§ 371 (c)(1),
(2) Date: Apr. 4, 2024

(87) PCT Pub. No.: WO2023/064196

PCT Pub. Date: Apr. 20, 2023

(65) Prior Publication Data

US 2024/0409531 A1 Dec. 12, 2024

Related U.S. Application Data

(60) Provisional application No. 63/256,194, filed on Oct. 15, 2021.

(51) Int. Cl.

| | |
|---|---|
| ***C07D 413/06*** | (2006.01) |
| ***A61K 31/538*** | (2006.01) |
| ***A61K 45/06*** | (2006.01) |
| ***C07D 265/36*** | (2006.01) |

(52) U.S. Cl.
CPC .......... *C07D 413/06* (2013.01); *A61K 31/538* (2013.01); *A61K 45/06* (2013.01); *C07D 265/36* (2013.01)

(58) Field of Classification Search
CPC .................................................. C07D 413/06
See application file for complete search history.

(56) References Cited

U.S. PATENT DOCUMENTS 5,874,430 A 2/1999 Christ et al.

FOREIGN PATENT DOCUMENTS

| | | |
|---|---|---|
| WO | 1994003440 A1 | 2/1994 |
| WO | 2022046844 A1 | 3/2022 |
| WO | 2022125412 A1 | 6/2022 |

OTHER PUBLICATIONS

Duchowicz, Pablo R. et al., QSAR for non-nucleoside inhibitors of HIV-1 reverse transcriptase, Bioorganic & Medicinal Chemistry, 14, 5876-5889, 2006.

Patel, Mona et al., Synthesis and evaluation of analogs of Efavirenz (SUSTIVA TM) as HIV-1 reverse transcriptase inhibitors, Bioorganic & Medicinal Chemistry Letters, 9, 2805-2810, 1999.

National Center for Biotechnology Information. br"(4S)-6-benzyl-4-(2-cyclopropylethynyl)-4-(trifluoromethyl)-1 H-3, 1-benzoxazin-2-one: Pubchem CID 155558621" Pubchem entry (online). Retrieved from the Internet: [URL: a href="https://pubchem.ncbi.nlm.nih.gov/compound/155558621" target="_blank"https://pubchem.ncbi.nlm.nih.gov/compound/155558621/a ]. Feb. 17, 2021; (retrieved on Nov. 30, 2022); p. 2, see 2D structure, 11 pages.

National Center for Biotechnology Information. br"6-[chloro-(2,3-difluorophenyl)methyl]-4H-1,4-benzoxazin-3-one: PUBCHEM CID 62659883" Pubchem entry (online). Retrieved from the Internet: [URL: bra href="https://pubchem.ncbi.nlm.nih.gov/compound/62659883" target="_blank"https://pubchem.ncbi.nlm.nih.gov/compound/62659883/a]. Oct. 22, 2012; (retrieved on Dec. 1, 2022); p. 2, see 2D structure, 9 pages.

National Center for Biotechnology Information. br"6-benzyl-4H-1,4-benzoxazin-3-one: PUBCHEM CID 11572255" Pubchem entry (online). Retrieved from the Internet: [URL: a href="https://pubchem.ncbi.nlm.nih.gov/compound/11572255" target="_blank"https://pubchem.ncbi.nlm.nih.gov/compound/11572255/a]. Oct. 26, 2006; (retrieved on Dec. 1, 2022); p. 2, see 2D structure, 10 pages.

*Primary Examiner* — Golam M Shameem

(74) *Attorney, Agent, or Firm* — Patricia A. Shatynski; John C. Todaro

(57) ABSTRACT

The present disclosure is directed to benzoxazinone derivatives of Formula I and their use for selectively killing HIV infected GAG-POL expressing cells without concomitant cytotoxicity to HIV naïve cells, and for the treatment or prophylaxis of infection by HIV, or for the treatment, prophylaxis or delay in the onset or progression of AIDS or AIDS Related Complex (ARC).

(I)

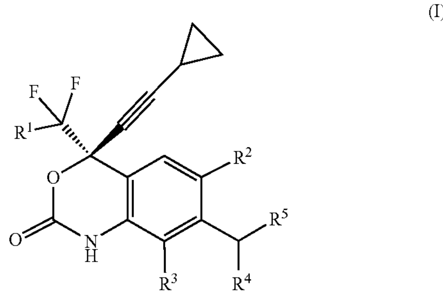

10 Claims, No Drawings

BENZOXAZINONE DERIVATIVES AS SELECTIVE CYTOTOXIC AGENTS

CROSS-REFERENCE TO RELATED APPLICATIONS

This application is a U.S. National Stage application of International Patent Application No. PCT/US2022/046143, filed Oct. 10, 2022, which claims priority to U.S. Provisional Application No. 63/256,194, filed Oct. 15, 2021, each of which is hereby incorporated by reference in its entirety.

BACKGROUND OF THE INVENTION

Human immunodeficiency virus (HIV) is the causative agent of acquired immunodeficiency syndrome (AIDS). In the absence of viral suppression, people living with HIV exhibit severe immunodeficiency which makes them highly susceptible to debilitating and ultimately fatal opportunistic infections. Multiple clinically approved antiretroviral drugs are available which demonstrate multi-log reductions in viral loads. Treated patients are at risk for acquiring mutations which render the virus in their bodies resistant to available therapies and rapid rebound of viremia is seen when therapy is removed, indicating that current regimens are not curative.

HIV is a retrovirus whose life cycle involves reverse transcription of a viral RNA genome into DNA via an enzyme known as reverse transcriptase and subsequent integration of the DNA copy into the host chromosomal DNA via the virally encoded integrase. Viral RNA is transcribed and viral proteins are translated using the host cellular machinery in conjunction with viral accessory proteins. Many viral proteins are contained within the GAG and GAG-POL polyproteins, with GAG containing structural proteins and GAG-POL resulting from a frameshift near the carboxy-terminus of GAG and containing protease (PR), reverse transcriptase (RT), and integrase (IN) viral enzymes, in addition to the structural proteins. GAG and GAG-POL are cleaved into individual proteins through the process of maturation which occurs during budding of virions from the infected cell. At this time GAG-POL dimerizes and the now dimeric HIV PR within the GAG-POL dimer forms an active enzyme which can cleave itself out of the polyprotein and catalyze further cleavage to form the remaining viral enzymes and structural proteins.

Available antiretroviral drugs act by blocking the virus at different stages in the viral life cycle. For example, reverse transcriptase inhibitors target the viral reverse transcriptase and prevent the RNA genome from being copied into DNA, integrase inhibitors block the ability of the copied DNA from being integrated into the host cell, and protease inhibitors prevent viral maturation so that virions produced from cells treated with protease inhibitors are immature and non-infectious. Once integration has occurred, a cell is infected until it dies through either normal cell death pathways, accelerated death due to viral factors, or is targeted by the immune system. While most infected cells are expected to die within ~2 days of being infected, the rapid rebound of viremia when therapy is removed is an indication that infected cells remain even after years on therapy (See, e.g., J. B. Dinoso et al., Proc. Natl. Acad. Sci. U.S.A., 2009, 106(23): 9403-9408). These latently infected and/or persistently virus-expressing cells that remain even during antiretroviral therapy are collectively termed the HIV reservoir and are the reason that people living with HIV require life-long treatment with a high level of adherence to maintain virus at undetectable levels. Thus, new therapies that can selectively kill the HIV infected cells would provide new treatment options for HIV infection. Treatment with compounds that can accelerate death of HIV infected cells and decrease the overall number of virally infected cells that persist within patients has the potential to decrease residual viremia in HIV suppressed individuals and address co-morbidities associated with chronic viral infection such as chronic inflammation, immune dysfunction, accelerated aging, cardiovascular disease (CVD), central nervous system (CNS) and other tissue and end-organ damage. Furthermore, treatment with compounds that can purge the remaining HIV reservoir may prolong viral remission off therapy and play a role in an HIV cure strategy.

SUMMARY OF THE INVENTION

The present disclosure is directed to benzoxazinone derivatives and their use as HIV-Targeted Activator of Cell Kill agents which accelerate the death of HIV GAG-POL expressing cells without concomitant cytotoxicity to HIV naïve cells. Accordingly, the compounds disclosed herein are useful for the treatment or prophylaxis of infection by HIV, or for the treatment, prophylaxis or delay in the onset or progression of AIDS or AIDS Related Complex (ARC). Additionally, the compounds are useful for selectively killing HIV infected, GAG-POL expressing cells in a subject infected with HIV. Compositions and methods of use comprising the compounds of this disclosure are also provided.

DETAILED DESCRIPTION OF THE INVENTION

The present disclosure is directed to benzoxazinone derivative compounds and their use for accelerating the death of HIV GAG-POL expressing cells without concomitant cytotoxicity to HIV naïve cells. In the absence of compounds such as those from the present invention, protease (PR) activation takes place during viral maturation and the concentration of mature PR in the cytoplasm is limited. In contrast, the present compounds promote the desired phenotype by catalyzing GAG-POL dimerization inside the infected cell by binding to the immature RT binding site and triggering premature activation of the HIV PR enzyme inside the host infected cell prior to budding. As a result, PR cleaves host substrates within the cell, leading to cytotoxicity and cell death. This effect can be blocked in the presence of an HIV protease inhibitor such as indinavir or darunavir demonstrating the role of HIV protease in the process.

The compounds presently disclosed herein also have activity as Non-Nucleoside Reverse Transcriptase Inhibitors (NNRTIs), due to the homology between the mature and immature RT pocket in HIV that allows the compounds to bind to the mature hydrophobic pocket near the active site of the viral RT enzyme. Binding to mature RT results in inhibition of enzymatic activity and production of the DNA provirus, which prevents infection of naïve CD4+ T-cells.

While effects of NNRTIs on dimerization of RT and GAG-POL have been documented (Tachedjian et al. Proc. Natl. Acad. Sci. U.S.A. 2001, 98(13):7188; Tachedjian et al. FEBS Lett. 2005, 579:379; Figueiredo et al. PLOS Path. 2006, 2(11):1051; Sudo et al. J. Virol. 2013, 87(6):3348), selective killing of HIV infected cells as a result of enhanced dimerization was first reported by Jochmans et al. (Jochmans et al. Retrovirology 2010, 7:89). The authors generated data showing these effects in chronically infected MT-4 cells, PBMCs, and CD4+ cells. Based on the potencies of tested molecules they concluded that "These data present proof of concept for targeted drug induced elimination of HIV producing cells. While NNRTIs themselves may not be sufficiently potent for therapeutic application, the results provide a basis for the development of drugs exploiting this mechanism of action." More recently, Zerbato et al. (Zerbato et al. Antimicrob. Agents Chemother. 2017, 61(3)) measured the activity of NNRTIs in a primary cell model for HIV latency. They saw significant reduction in virus production for certain NNRTIs compared to other classes of antiretrovirals and inferred that this was due to these compounds' ability to eliminate cells expressing HIV GAG-POL proteins. More recently, in their paper Trinitd et al. (Trinitd et al., Retrovirology, 2019, 16(17)) stated that NNRTI-induced PR-activation triggers apoptotic cell death of productively HIV-infected resting or activated T-cells.

The present disclosure is directed to a compound of Formula I

I

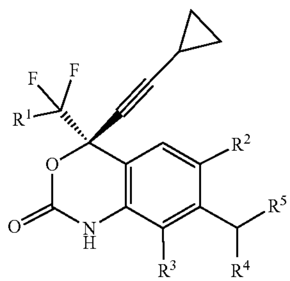

or a pharmaceutically acceptable salt thereof, wherein:

$R^1$ is halo or —$C_{1-8}$alkyl unsubstituted or substituted with 1 to 7 of —F (F or $CH_3$);

$R^2$ is —H, halo, —CN, —$C_{1-8}$alkyl, —$C_{2-8}$alkenyl, —C(O)O$C_{1-8}$alkyl, —C(O)$C_{1-8}$alkyl or —$NR^6R^7$;

$R^3$ is —H or halo;

$R^4$ is —H or halo;

$R^5$ is a 5 or 6-membered ring selected from phenyl, pyrimidinyl, pyrimidinone, pyrazinone, pyrazolyl and pyridinyl, wherein each ring is unsubstituted or substituted with one or more substituents up to the maximum number allowed by valence, independently selected at each occurrence from:

(i) halo, (ii) —CN, (iii) —$NR^6R^7$, (iv) —$SO_2$—$NR^6R^7$, (v) —$C_{1-8}$alkyl unsubstituted or substituted with 1 to 8 substituents independently selected at each occurrence from —OH and halo, (vi) —$C_{1-4}$alkyl-O—$C_{1-4}$alkyl unsubstituted or substituted with 1 to 8 substituents independently selected at each occurrence from —OH or halo, and (vii) —O$C_{1-8}$alkyl unsubstituted or substituted with 1 to 8 substituents independently selected at each occurrence from —OH and halo;

$R^6$ is —H or —$C_{1-8}$alkyl unsubstituted or substituted with 1 to 8 substituents independently selected at each occurrence from —OH and halo; and $R^7$ is —H or —$C_{1-8}$alkyl unsubstituted or substituted with 1 to 8 substituents independently selected at each occurrence from —OH and halo.

In Embodiment 1 of this disclosure are compounds of Formula I, or pharmaceutically acceptable salts of the foregoing, wherein $R^1$ is halo or —$C_{1-6}$alkyl; or in a class thereof $R^1$ is F, Cl, Br or $C_{1-3}$alkyl; or in a further class thereof $R^1$ is F or —$CH_3$.

In Embodiment 2 of this disclosure are compounds of Formula I and Embodiment 1, and each class thereof, or pharmaceutically acceptable salts of the foregoing, wherein $R^2$ is —H, halo, —CN, —$C_{1-6}$alkyl, —$C_{2-6}$alkenyl, —C(O)O—$C_{1-6}$alkyl, —C(O)—$C_{1-6}$alkyl, or —$NR^6R^7$. In a class thereof $R^2$ is —H, F, Cl, Br, —CN, —$C_{1-3}$alkyl, —C(O)O—$C_{1-3}$alkyl, —C(O)—$C_{1-3}$alkyl or —$NR^6R^7$. In a further class thereof $R^2$ is —H, F, Cl, Br or —$CH_3$; and in a further class thereof $R^2$ is —H, F or $C_1$.

In Embodiment 3 of this disclosure are compounds of Formula I, Embodiment 1 or Embodiment 2, and each class thereof, or pharmaceutically acceptable salts of the foregoing, wherein $R^3$ is —H, F, Cl or Br. In a further class thereof $R^3$ is —H or F; or $R^3$ is —H.

In Embodiment 4 of this disclosure are compounds of Formula I, Embodiment 1, Embodiment 2 or Embodiment 3, and each class thereof, or pharmaceutically acceptable salts of the foregoing, wherein $R^4$ is —H, F, Cl or Br. In a further class thereof $R^4$ is —H or F; or $R^4$ is —H.

In Embodiment 5 of this disclosure are compounds of Formula I, Embodiment 1, Embodiment 2, Embodiment 3 or Embodiment 4, and each class thereof, or pharmaceutically acceptable salts of the foregoing, wherein $R^6$ and $R^7$ are each independently selected from —H and —$C_{1-6}$alkyl. In a class thereof, $R^6$ and $R^7$ are each independently selected from —H and —$C_{1-3}$alkyl. In a further class thereof, $R^6$ and $R^7$ are each independently selected from —H and $CH_3$; or $R^6$ and $R^7$ are each —H.

In Embodiment 6 of this disclosure are compounds of Formula I, Embodiment 1, Embodiment 2, Embodiment 3, Embodiment 4 or Embodiment 5, and each class thereof, or pharmaceutically acceptable salts of the foregoing, wherein $R^5$ is selected from:

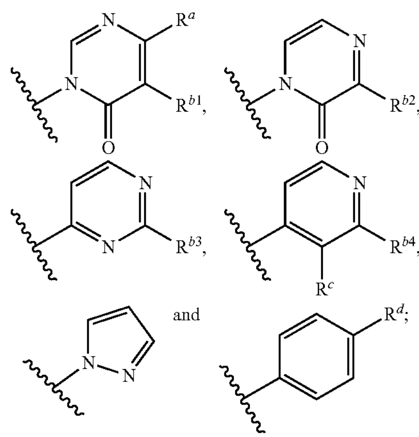

wherein:

$R^a$ is (i) —H, (ii) —$C_{1-6}$alkyl (e.g., —$C_{1-3}$alkyl or —$CH_3$), (iii) —$C_{1-3}$alkyl substituted with 1-7 of halo (e.g., —$CH_2F$, $CHF_2$ or —$CF_3$), (iv) —$C_{1-3}$alkyl-O—$C_{1-3}$alkyl (e.g., —$CH_2$—O—$CH_3$), or (v) —O$C_{1-6}$alkyl (e.g., —O$C_{1-3}$alkyl or —O$CH_3$);

$R^{b1}$, $R^{b2}$, $R^{b3}$ and $R^{b4}$ are each independently selected from (i) —H or (ii) —$NR^6R^7$ (e.g., —$NH_2$);

$R^c$ is (i) —H, (ii) halo (e.g., —F or —$C_1$) or (iii) —CN;

$R^d$ is (i) —$C_{1-6}$alkyl (e.g., —$C_{1-3}$alkyl or —$CH_3$), (ii) —$C_{1-3}$alkyl substituted with 1-7 of halo (e.g., —$CH_2F$, $CHF_2$ or —$CF_3$), or (iii) —$S(O)_2NR^6R^7$ (e.g., —$S(O)_2NH_2$).

In Embodiment 7 are compounds of Formula I, or pharmaceutically acceptable salts thereof, wherein:

$R^{b1}$, $R^{b2}$, $R^{b3}$ and $R^{b4}$ are each independently selected from —F or $CH_3$;

$R^2$ is —H, —F, —$C_1$, —CN or —$C_{1-3}$alkyl; or $R^2$ is —H, —F or —$C_1$;

$R^3$ is —H or halo; or $R^3$ is —H; and $R^4$ is —H or halo; or $R^4$ is —H.

In Embodiment 8 Formula I, Embodiment 1, Embodiment 2, Embodiment 3, Embodiment 4 or Embodiment 5, and each class thereof, or pharmaceutically acceptable salts of the foregoing, wherein:

$R^5$ is selected from:

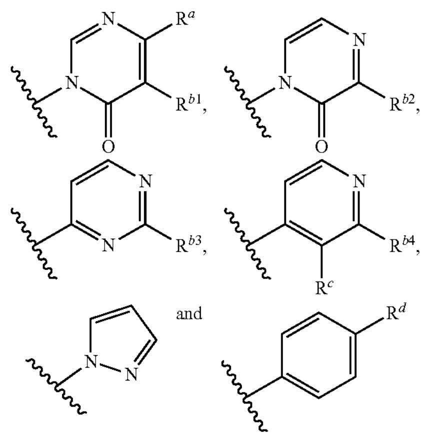

and wherein:

$R^a$ is (i) —H, (ii) —$C_{1-3}$alkyl (e.g., —$CH_3$), (iii) —$CH_2F$, —$CHF_2$ or —$CF_3$, (iv) —$CH_2$—O—$CH_3$, or (v) —$OC_{1-3}$alkyl (e.g., —$OCH_3$);

$R^{b1}$, $R^{b2}$, $R^{b3}$ and $R^{b4}$ are each independently selected from —H or —$NH_2$;

$R^c$ is —H or —CN; and $R^d$ is (i) —$C_{1-3}$alkyl (e.g. —$CH_3$), (ii) —$CH_2F$, $CHF_2$ or —$CF_3$, or (iii) —$S(O)_2NH_2$.

The invention is directed to the compounds of Formula I herein and all embodiments, examples, classes and subclasses thereof and includes the compounds of the Examples herein. The invention is further directed to compounds of Formula I which are neutral compounds or salts thereof when such salts are possible, including pharmaceutically acceptable salts.

The term "e.g." means "for example." When the terms "e.g.," or "for example" are used herein, the example(s) recited are intended to be illustrative and are not intended to be an exhaustive list of all relevant examples. The term "i.e." means "that is."

As used herein, "alkyl" refers to both branched- and straight-chain saturated aliphatic hydrocarbon groups having the specified number of carbon atoms in a specified range. For example, "$C_{1-8}$alkyl" refers to each of the alkyl groups having 1, 2, 3, 4, 5, 6, 7, or 8 carbon atoms, including linear or branched isomers thereof. "$C_{1-8}$alkyl" includes the "$C_{1-6}$alkyl" groups and the linear and branched chain alkyls having 7 or 8 carbons in the chain.

The term "$C_{1-6}$alkyl" means each of the linear or branched chain alkyl groups, including all or each of the possible isomers, having 1, 2, 3, 4, 5 or 6 carbon atoms, and includes each of the hexyl and pentyl isomers as well as n-, iso-, sec- and tert-butyl (butyl, i-butyl, s-butyl, t-butyl, collectively "$C_4$alkyl"; Bu=butyl), n- and i-propyl (propyl, i-propyl, collectively "$C_3$alkyl"; Pr=propyl), ethyl (Et) and methyl (Me). "$C_{1-4}$alkyl" has 1, 2, 3 or 4 carbon atoms and includes each of n-, i-, s- and t-butyl, n- and i-propyl, ethyl and methyl. "$C_{1-3}$alkyl" has 1, 2 or 3 carbon atoms and includes each of n-propyl, i-propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" refers to all or each of the hexenyl and pentenyl isomers as well as 1-butenyl, 2-butenyl, 3-butenyl, isobutenyl, 1-propenyl, 2-propenyl, and ethenyl (or vinyl). "$C_{2-8}$alkenyl" includes the "$C_{2-6}$ alkenyl" groups plus the linear and branched chain alkenyls having 7 or 8 carbons in the chain.

"Halo" or "halogen" refers to chloro, fluoro, bromo and/or iodo. Chloro, fluoro and bromo are a class of halogens of interest, and more particularly fluoro and chloro.

"HIV naïve cell(s)" are cells that are not infected with HIV.

"Compatible anti-HIV agent(s)" are anti-HIV agents excluding HIV protease inhibitors.

A "latency reversing agent" (LRA) is a pharmaceutical agent capable of re-activating latent HIV (e.g., HIV-1) in an HIV (e.g., HIV-1) infected cell, particularly in a human.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present disclosure are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

This disclosure includes individual diastereomers, particularly epimers, i.e., compounds having the same chemical formula but which differ in the spatial arrangement around a single atom. This disclosure also includes mixtures of diastereomers, particularly mixtures of epimers, in all ratios. This disclosure encompasses compounds of Formula I having either the (R) or (S) stereo-configuration at an asymmetric center and at any additional asymmetric centers that may be present in a compound of Formula I, as well as stereo-isomeric mixtures thereof. Embodiments of this disclosure also include a mixture of enantiomers enriched with 51% or more of one of the enantiomers, including for example 60% or more, 70% or more, 80% or more, or 90% or more of one enantiomer. A single epimer is preferred. An individual or single enantiomer refers to an enantiomer obtained by chiral synthesis and/or using generally known separation and purification techniques, and which may be 100% of one enantiomer or may contain small amounts (e.g., 10% or less) of the opposite enantiomer. Thus, individual enantiomers are a subject of this disclosure in pure form, both as levorotatory and as dextrorotatory antipodes, in the form of racemates and in the form of mixtures of the two enantiomers in all ratios. In the case of a cis/trans isomerism this disclosure includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present disclosure includes all such isomers, as well as salts, solvates (which includes hydrates), and solvated salts of such racemates, enantiomers, diastereomers and tautomers and mixtures thereof.

As would be recognized by one of ordinary skill in the art, certain compounds of the present disclosure may be able to exist as tautomers. All tautomeric forms of such compounds, whether isolated individually or in mixtures, are within the scope of the present disclosure. For example, in instances where an amine ($—NH_2$) substituent is permitted on a heterocyclic ring and amino-imino tautomerism is possible, it is understood that the substituent might in fact be present, in whole or in part, in the ═NH form.

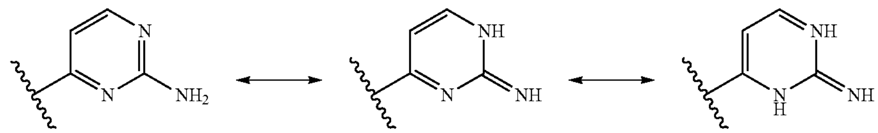 [SMILES: *c1ccnc(N)n1 ; *c1cc[nH]c(=N)n1 ; *c1ccnc(=N)[nH]1]

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of Formula I; for example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). When the compounds of Formula I contain one or more acidic groups or basic groups, the invention includes the corresponding pharmaceutically acceptable salts.

Thus, the compounds of Formula I that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids.

Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

The instant disclosure encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

Furthermore, compounds of the present disclosure may exist in amorphous form and/or one or more crystalline forms, and as such all amorphous and crystalline forms and mixtures thereof of the compounds of Formula I and salts thereof are intended to be included within the scope of the present disclosure. In addition, some of the compounds of the instant disclosure may form solvates with water (i.e., a hydrate) or common organic solvents. Such solvates and hydrates, particularly the pharmaceutically acceptable solvates and hydrates, of the compounds of this disclosure are likewise encompassed within the scope of the compounds defined by Formula I and the pharmaceutically acceptable salts thereof, along with un-solvated and anhydrous forms of such compounds.

Accordingly, the invention is directed to compounds of Formula I or salts thereof including pharmaceutically acceptable salts thereof, embodiments thereof and specific compounds described and claimed herein, and encompass all possible stereoisomers, tautomers, physical forms (e.g., amorphous and crystalline forms), co-crystal forms, solvate and hydrate forms, and any combination of the foregoing forms where such forms are possible.

Another embodiment of the present disclosure is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for eliciting GAG-POL dimerization in HIV-infected cells and thereby selectively killing HIV infected GAG-POL expressing cells without concomitant cytotoxicity to HIV naïve cells, referred to herein as TACK (Targeted Activator of Cell Kill) activity, or more specifically HIV TACK activity. HIV TACK or TACK have also been previously referred to as Small Molecule Activated Cell Kill (SMACK). Thus, the compounds of Formula I and pharmaceutically acceptable salts thereof are useful for:

(i) A method for the treatment or prophylaxis of infection by HIV, or for the treatment, prophylaxis, or delay in the onset or progression of AIDS or ARC in a human subject in need thereof which comprises administering to the human subject an effective amount of the compound according to Formula I, or a pharmaceutically acceptable salt thereof; and/or (ii) A method for eliciting GAG-POL dimerization in HIV-infected cells in a human subject in need thereof which comprises administering to the human subject an effective amount of the compound according to Formula I, or a pharmaceutically acceptable salt thereof; and/or (iii) A method for selectively killing HIV infected GAG-POL expressing cells without concomitant cytotoxicity to HIV naïve cells in a human subject which comprises administering to the human subject an effective amount of the compound according to Formula I, or a pharmaceutically acceptable salt thereof; and/or (iv) A method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Additionally, the compounds of Formula I and pharmaceutically acceptable salts thereof are useful for any of the methods (i), (ii), (iii) or (iv) above, further comprising administering to the human subject an effective amount of one or more compatible HIV antiviral agents selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents. In the methods of (i), (ii), (iii) or (iv) immediately above, the human subject can be treated with a compound of Formula I or a pharmaceutically acceptable salt thereof in addition to treatment with one or more compatible HIV antiviral agents.

The compounds of Formula I and pharmaceutically acceptable salts thereof are also useful for a method for augmenting the suppression of HIV viremia in a human subject whose viremia is being suppressed by administration of one or more compatible HIV antiviral agents, which comprises additionally administering to the human subject an effective amount of the compound according to Formula I, or a pharmaceutically acceptable salt thereof.

Other embodiments of the present disclosure include the following:

(a) A pharmaceutical composition comprising an effective amount of a compound of Formula I or a pharmaceutically acceptable salt thereof, and a pharmaceutically acceptable carrier.

(b) A pharmaceutical composition which comprises the product prepared by combining (e.g., mixing) an effective amount of a compound of Formula I or a pharmaceutically acceptable salt thereof, and a pharmaceutically acceptable carrier.

(c) The pharmaceutical composition of (a) or (b), further comprising an effective amount of one or more compatible anti-HIV agents selected from the group consisting of HIV antiviral agents, immunomodulators, anti-infective agents and latency reversing agents.

(d) The pharmaceutical composition of (c), wherein the compatible anti-HIV agent is selected from one or more of an antiviral selected from the group consisting of nucleoside or nucleotide HIV reverse transcriptase inhibitors, nucleoside HIV reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(e) A combination which is (i) a compound of Formula I or a pharmaceutically acceptable salt thereof and (ii) one or more compatible anti-HIV agents selected from the group consisting of HIV antiviral agents, immunomodulators, anti-infective agents and latency reversing agents; wherein the compound and the compatible anti-HIV agent are each employed in an amount that renders the combination effective for the treatment or prophylaxis of infection by HIV, or for the treatment, prophylaxis or delay in the onset or progression of AIDS or ARC.

(f) The combination of (e), wherein the compatible anti-HIV agent is an antiviral selected from the group consisting of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(g) A method for eliciting GAG-POL dimerization in HIV-infected cells, a method for selectively killing HIV infected GAG-POL expressing cells without concomitant cytotoxicity to HIV naïve cells, and/or a method for the treatment or prophylaxis of infection by HIV, or for the treatment, prophylaxis, or delay in the onset or progression of AIDS or ARC, comprising administering an effective amount of a compound of Formula I or a pharmaceutically acceptable salt thereof to a subject in need of such treatment.

(h) The method of (g), wherein the compound of Formula I or a pharmaceutically acceptable salt thereof is administered in combination with an effective amount of at least one other compatible HIV antiviral selected from nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

(i) The method of (g) or (h) comprising administering to the subject the pharmaceutical composition of (a), (b), (c) or (d) or the combination of (e) or (f).

(j) Use of a compound of Formula I or a pharmaceutically acceptable salt thereof in the manufacture of a medicament for (1) eliciting GAG-POL dimerization in HIV-infected cells in a subject; (2) selectively killing HIV infected GAG-POL expressing cells without concomitant cytotoxicity to HIV naïve cells in a subject; (3) treatment or prophylaxis of infection by HIV in a subject; (4) treatment, prophylaxis or delay in the onset or progression of AIDS or ARC in a subject; (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

(k) A compound of Formula I, or a pharmaceutically acceptable salt thereof, for use in (1) eliciting GAG-POL dimerization in HIV-infected cells; (2) selectively killing HIV infected GAG-POL expressing cells without concomitant cytotoxicity to HIV naïve cells; (3) treatment or prophylaxis of infection by HIV; (4) the treatment, prophylaxis or delay in the onset or progression of AIDS or ARC; and/or (5) augmenting the suppression of HIV viremia in a subject undergoing treatment with a compatible anti-HIV agent, and/or (6) augmenting the suppression of HIV viremia in a subject whose viremia is being suppressed by administration of one or more compatible HIV antiviral agents.

Additional embodiments of the present invention include each of the pharmaceutical compositions, methods and uses set forth in the preceding paragraphs, wherein the compound of Formula I or its salt employed therein is substantially pure. With respect to a pharmaceutical composition comprising a compound of Formula I or its salt and a pharmaceutically acceptable carrier and optionally one or more excipients, it is understood that the term “substantially pure” is in reference to a compound of Formula I or its salt per se.

In another embodiment of the present disclosure are the pharmaceutical compositions, methods, medicaments, uses and combinations set forth herein, wherein the HIV of interest is HIV-1. Thus, for example, in any of the pharmaceutical compositions, methods, medicaments, uses and combinations using the compounds of Formula I or pharmaceutically acceptable salts thereof, the compound or salt thereof is employed in an amount effective against HIV-1; and when used in combination with one or more compatible anti-HIV agent(s), each such additional agent is a compatible HIV-1 antiviral selected from, for example but not limited to, one or more of nucleoside or nucleotide HIV reverse transcriptase inhibitors, nucleoside reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

The term “administration” and variants thereof (e.g., “administering” a compound) in reference to a compound of Formula I means providing the compound to the individual in need of treatment or prophylaxis and includes both self-administration and administration to the patient by another person or any other means. When a compound is provided in combination with one or more other active agents (e.g., antiviral agents useful for treating or prophylaxis of HIV infection or AIDS), “administration” and its variants are each understood to include provision of the compound and other agents at the same time or at different times. When the agents of a combination are administered at the same time, they can be administered together in a single composition or they can be administered separately.

As used herein, the term “composition” is intended to encompass a product comprising the specified ingredients, as well as any product which results from combining the specified ingredients. Ingredients suitable for inclusion in a pharmaceutical composition are pharmaceutically acceptable ingredients, which means the ingredients must be compatible with each other and not deleterious to the recipient thereof.

The term “subject” or “patient” as used herein refers to a human (or “person”) who has been the object of treatment, observation or experiment. Examples of patients to be treated with an HIV TACK agent include but are not limited to, patients who have been infected with HIV, and/or HIV infected patients whose HIV viral load has been suppressed and/or is considered to be undetectable at time of HIV TACK treatment. Patients to be treated with an HIV TACK agent also include, but are not limited to, those using an HIV TACK agent for prophylaxis of HIV infection or for post-exposure prophylaxis after being potentially exposed to HIV to prevent becoming infected.

"Prophylaxis" includes each of pre-exposure prophylaxis (PrEP), i.e., using a compound of Formula I or a pharmaceutically acceptable salt thereof to prevent HIV infection in a person who does not have HIV, and post-exposure prophylaxis (PEP), i.e., using a compound of Formula I or a pharmaceutically acceptable salt thereof after being potentially exposed to HIV to prevent becoming infected with HIV.

The term "effective amount" as used herein means an amount of a compound sufficient to elicit GAG-POL dimerization in HIV-infected cells and selectively kill HIV infected GAG-POL expressing cells without concomitant cytotoxicity to HIV naïve cells; and/or exert a therapeutic effect, and/or exert a prophylactic effect after administration. One embodiment of "effective amount" is a "therapeutically effective amount" which is an amount of a compound that is effective for selectively killing HIV infected GAG-POL expressing cells, effective for treating HIV infection, or effective for the treatment, prophylaxis or delay in the onset or progression of AIDS or ARC in a patient infected with HIV. Another embodiment of "effective amount" is a "prophylactically effective amount" which is an amount of the compound that is effective for prophylaxis of HIV infection, or prophylaxis of AIDS or ARC in an HIV-infected patient. It is understood that an effective amount can simultaneously be both a therapeutically effective amount, e.g., for treatment of HIV infection, and a prophylactically effective amount, e.g., for prevention or reduction of risk for developing AIDS or ARC in a subject infected with HIV.

In the combination therapies of the present invention, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

In the methods of the present invention, (i.e., selectively killing HIV infected GAG-POL expressing cells, the treatment of infection by HIV, prophylaxis of HIV infection or the treatment, prophylaxis or delay in the onset or progression of AIDS or ARC and other methods described herein), the compounds of this invention, or salts thereof, can be administered by means that produce contact of the active agent with the agent's site of action. They can be administered by conventional means available for use in conjunction with pharmaceuticals, either as individual therapeutic agents or in a combination of therapeutic agents. The compound can be administered itself, but typically is administered with a pharmaceutical carrier selected on the basis of the chosen route of administration and standard pharmaceutical practice. The compounds of the invention can, for example, be administered orally (e.g., via tablet or capsule), parenterally (including subcutaneous injections, intravenous, intramuscular or intrasternal injection, or infusion techniques), by inhalation spray, or rectally, in the form of a unit dosage of a pharmaceutical composition containing an effective amount of the compound and conventional non-toxic pharmaceutically acceptable carriers, adjuvants and vehicles. The compound could also be administered via an implantable drug delivery device adapted to provide an effective amount of the compound or a pharmaceutical composition of the compound over an extended period of time.

Formulations

Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Liquid preparations suitable for oral administration (e.g., suspensions, syrups, elixirs and the like) can be prepared according to techniques known in the art and can employ any of the usual media such as water, glycols, oils, alcohols and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Implantable compositions can be prepared according to methods known in the art wherein the carrier comprises the active chemical ingredient with polymers and suitable excipients, or utilizing an implantable device for drug delivery. Further description of methods suitable for use in preparing pharmaceutical compositions for use in the present invention and of ingredients suitable for use in said compositions is provided in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Formulations of compounds of Formula I that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp. 631-644 (2007)).

The compounds of Formula I may be administered in a dosage range of, e.g., 1 to 20 mg/kg, or 1 to 10 mg/kg, or about 5 mg/kg of mammal (e.g., human) body weight per day, or at other time intervals as appropriate, in a single dose or in divided doses. The compounds of Formula I may be administered in a dosage range of 0.001 to 2000 mg. per day in a single dose or in divided doses. Examples of dosage ranges are 0.01 to 1500 mg per day, or 0.1 to 1000 mg per day, administered orally or via other routes of administration in a single dose or in divided doses.

For oral (e.g., tablets or capsules) or other routes of administration, the dosage units may contain 100 mg to 1500 mg of the active ingredient, for example but not limited to, 100, 150, 200, 250, 300, 350, 400, 450, 500, 600, 700, 800, 900, 1000, 1100, 1200, 1300, 1400 or 1500 milligrams of the active ingredient for the symptomatic adjustment of the dosage to the patient to be treated. Furthermore, the compound may be formulated in oral formulations for immediate or modified release such as extended or controlled release. When the compound of Formula I is administered as a salt, reference to an amount of the compound in milligrams or grams is based on the free form (i.e., the non-salt form) of the compound.

Daily administration can be via any suitable route of administration but is preferably via oral administration and can be a single dose or more than one dose at staggered times (divided daily doses) within each 24-hour period. Each dose may be administered using one or multiple dosage units as appropriate.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In some cases, depending on the potency of the compound or the individual response, it may be necessary to deviate upwards or downwards from the given dose. The amount and frequency of administration will be regulated according to the judgment of the attending clinician considering such factors.

An "anti-HIV agent" is any agent which is directly or indirectly effective in the inhibition of HIV, the treatment or prophylaxis of HIV infection, and/or the treatment, prophylaxis or delay in the onset or progression of AIDS or ARC. It is understood that an anti-HIV agent is effective in treating, preventing, or delaying the onset or progression of HIV infection or AIDS and/or diseases or conditions arising therefrom or associated therewith. The present disclosure is additionally directed to use of a compound of Formula I or pharmaceutically acceptable salts thereof, with one or more compatible anti-HIV agents, i.e., anti-HIV agents excluding HIV protease inhibitors (also referred to as "compatible HIV antivirals"). For example, the compounds of Formula I may be administered in combination with effective amounts of one or more compatible anti-HIV agents selected from HIV antiviral agents, immunomodulators, anti-infectives, or vaccines useful for treating HIV infection or AIDS. Suitable compatible HIV antivirals for use in combination with the compounds of the present disclosure include, but are not limited to, those listed in Table A as follows:

TABLE A

Antiviral Agents for Treating HIV infection or AIDS

| Name | Type |
|---|---|
| abacavir, ABC, ZIAGEN ® | NRTI |
| abacavir + lamivudine, EPZICOM ® | NRTI |
| abacavir + lamivudine + zidovudine, TRIZIVIR ® | NRTI |
| AZT, zidovudine, azidothymidine, RETROVIR ® | NRTI |
| bictegravir | InSTI |
| bictegravir + tenofovir alafenamide fumarate + emtricitabine, BIKTARVY ® | InSTI/NRTI/NRTI |
| capravirine | NNRTI |
| cabotegravir | InSTI |
| Cabotegravir + rilpivirine, CABENUVA | InSTI/NNRTI |
| ddC, zalcitabine, dideoxycytidine, HIVID ® | NRTI |
| ddI, didanosine, dideoxyinosine, Videx ® | NRTI |
| ddI (enteric coated), VIDEX EC ® | NRTI |
| delavirdine, DLV, RESCRIPTOR ® | NNRTI |
| Dolutegravir + lamivudine, DOVATOR ® | InSTI/NRTI |
| Dolutegravir + rilpivirine, JULUCA ® | InSTI/NNRTI |
| dolutegravir, TIVICAY ® | InSTI |
| dolutegravir + abacavir + lamivudine, TRIUMEQ ® | InSTI/NRTI/NRTI |
| doravirine, PIFELTRO ™ | NNRTI |
| doravirine/lamivudine/tenofovir disoproxil fumarate, DELSTRIGO ™ | NNRTI/NRTI/NRTI |
| efavirenz, EFV, SUSTIVA ®, STOCRIN ® | NNRTI |
| Efavirenz/emtricitabine/tenofovir disoproxil fumarate, ATRIPLA ® | NNRTI/NRTI/NRTI |
| Islatravir, (4'-ethynyl-2-fluoro-2'-deoxyadenosine; EFdA) | NRTTI |
| Elvitegravir, VITEKTA ® | InSTI |
| emtricitabine, FTC, EMTRIVA ® | NRTI |

TABLE A-continued

Antiviral Agents for Treating HIV infection or AIDS

| Name | Type |
|---|---|
| emtricitabine + tenofovir alafenamide fumarate, DESCOVY ® | NRTI/NRTI |
| emtricitabine + tenofovir disoproxil fumarate, TRUVADA ® | NRTI/NRTI |
| emivirine, COACTINON ® | NNRTI |
| enfuvirtide, FUZEON ® | FI |
| enteric coated didanosine, VIDEX EC ® | NRTI |
| etravirine, TMC-125 | NNRTI |
| Fostemsavir, RUKOBIA ® | AI |
| Ibalizumab-uiyk (TROGARZO ®) | Post-Attachment Inhibitor or Monoclonal Antibody |
| lamivudine, 3TC, EPIVIR ® | NRTI |
| lamivudine + zidovudine, COMBIVIR ® | NRTI/NRTI |
| lenacapavir | Capsid inhibitor |
| maraviroc, SELZENTRY ® | EI |
| nevirapine, NVP, VIRAMUNE ® | NNRTI |
| raltegravir, ISENTRESS ™ | InSTI |
| rilpivirine, EDURANT ® | NNRTI |
| stavudine, d4T,didehydrodeoxythymidine, ZERIT ® | NRTI |
| tenofovir disoproxil fumarate (TDF), VIREAD ® | NRTI |
| tenofovir alafenamide fumarate (TAF) | NRTI |
| vicriviroc | EI |

AI = attachment inhibitor;
EI = entry inhibitor;
FI = fusion inhibitor;
InSTI = integrase inhibitor;
NRTI = nucleoside or nucleotide reverse transcriptase inhibitor;
NNRTI = non-nucleoside reverse transcriptase inhibitor;
NRTTI = nucleoside reverse transcriptase translocation inhibitor. Some of the drugs listed in Table A are used form; e.g., abacavir sulfate, delavirdine mesylate.

The TACK effect elicited by an HIV-TACK agent depends on expression of viral Gag-Pol. Therefore additional active agents, such as latency reversing agents ("LRA" or "LRAs"), that enhance Gag-Pol production in infected cells and/or activate viral expression in cells that comprise the latent HIV reservoir, when used together with HIV-TACK therapy, are likely to enhance the TACK effect. The present disclosure is additionally directed to use of a compound of Formula I, or a pharmaceutically acceptable salt thereof, with one or more LRA(s). For example, the compounds of Formula I may be administered in combination with effective amounts of one or more LRA(s) for treatment of HIV infection or AIDS. Examples of LRAs for use in combination with the compounds of the present disclosure include, but are not limited to epigenetic modifiers such as histone deacetylase (HDAC) inhibitors, DNA methyltransferase (DNMT) inhibitors, and histone methyltransferase (HMT) inhibitors; Protein Kinase C (PKC) agonists such as prostratins, bryostatins, or ingenols; inducers of P-TEFb release such as BET inhibitors (e.g., JQ1 or a class of drugs that reversibly bind the bromodomains of Bromodomain and Extra-Terminal motif (BET) proteins BRD2, BRD3, BRD4, and/or BRDT), antagonists of C—C chemokine receptor type 5 (CCR5), inducers of non-canonical NF-κB pathway (e.g., second mitochondria-derived activator of caspases (SMAC) mimetics or inhibitor of apoptosis proteins (IAP) antagonists, proteasome inhibitors, toll-like receptor (TLR) agonists, mitogen-activated protein kinase (MAPK) agonists, Ak strain transforming/protein kinase B (AKT/PKB) pathway activators, cytokines and immunomodulatory agents such as immune checkpoint inhibitors and those described elsewhere such as Bullen et al, Nature Medicine, 20:425-429 (2014); Ait-Ammar et al, Frontiers in Microbiology, 10:3060 (2019); and Fujinaga et al, Viruses. 12:11 (2020).

Examples of HDAC inhibitors that can be used as latency reversing agents include, but are not limited to, vorinostat, panabinostat, romidepsin, and valproic acid. Examples of DNMT inhibitors that can be used as latency reversing agents include, but are not limited to, 5-aza-2'-cytidine and 5-aza-2'-deoxycytidine. Examples of HMT inhibitors that can be used as latency reversing agents include, but are not limited to, chaetocin, 3-deazaneplanocin A, tazemetostat (EPZ-6438), N-[(1,2-dihydro-6-methyl-2-oxo-4-propyl-3-pyridinyl)methyl]-1-(1-methylethyl)-6-[2-(4-methyl-1-piperazinyl)-4-pyridinyl]-1H-indazole-4-carboxamide (GSK-343) and 2-cyclohexyl-6-methoxy-N-[1-(1-methylethyl)-4-piperidinyl]-7-[3-(1-pyrrolidinyl)propoxy]-4-quinazolinamine (UNC-0638). Examples PKC agonists that can be used as latency reversing agents include, but are not limited to, phorbolesters such as prostratin and phorbol myristate acetate (PMA), bryostatin-1, and ingenol. Examples of BET inhibitors that can be used as a latency reversing agents include, but are not limited to, JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate), iBET, and N-cyclohexyl-2-(4-(3,5-dimethylisoxazol-4-yl)-2-methoxyphenyl)imidazo[1,2-a]pyrazin-3-amine (UMB-136). An example of a CCR5 antagonist that can be used as latency reversing agent includes, but is not limited to, maraviroc and vicriviroc. Examples of inducers of the non-canonical NF-κB pathway and SMAC mimetics/IAP inhibitors that can be used as latency reversing agents include, but are not limited to, 3,3'-[2,4-hexadiyne-1,6-diylbis[oxy[(1S,2R)-2,3-dihydro-1H-indene-2,1-diyl]]]bis[N-methyl-L-alanyl-(2S)-2-cyclohexglycyl-L-prolinamide (AZD5582), Ciapavir, Birinapant, LCL161, and DEBIO1143/AT-406. Examples of proteasome inhibitors that can be used as latency reversing agents include, but are not limited to, bortezomib and ixazomib. Examples of TLR agonists that can be used as latency reversing agents include, but are not limited to, the TLR2 agonist Pam3CSK4, the TLR7 agonist vesatolimod, and the TLR9 agonists Lefitolimod (MGN1703) and CPG 7909.

An example of an MAPK agonist that can be used as a latency reversing agent includes, but is not limited to, procyanidin trimer $C_1$. An example of an AKT pathway activator that can be used as latency reversing agent includes, but is not limited to, disulfiram. Examples of immunomodulatory cytokines that can be used as latency reversing agents include, but are not limited to, IL-2, IL-7, and IL-15, including the IL-15 superagonist N-803. Examples of immune checkpoint inhibitors include, but are not limited to, inhibitors of Programmed cell death protein 1 (PD1), Programmed death-ligand 1 (PD-L1) inhibitors, cytotoxic T-lymphocyte-associated protein 4 (CTLA-4), Lymphocyte-activation gene 3 (LAG3), T cell immunoreceptor with Ig and MM domains) (TIGIT) and CD24Fc, a recombinant fusion protein composed of the extracellular domain of the mature human glycoprotein cluster of differentiation 24 (CD24) linked to a human immunoglobulin G1 (IgG1) Fc domain.

Thus, the compounds of Formula I, or pharmaceutically acceptable salts thereof, used together with a latency reversing agent can be useful for:

(i) A method for re-activating latent HIV and eliciting GAG-POL dimerization in HIV-infected cells (e.g., CD4 T cells) in a human subject which comprises administering to the subject an effective amount of a compound according to Formula I, or a pharmaceutically acceptable salt thereof, and a latency reversing agent; and/or (ii) A method for re-activating latent HIV and selectively killing HIV-infected GAG-POL expressing cells (e.g., latently HIV-infected CD4 T cells or central memory CD4 T cells), without concomitant cytotoxicity to HIV naïve cells, in a human subject which comprises administering to the subject an effective amount of a compound according to Formula I, or a pharmaceutically acceptable salt thereof, and a latency reversing agent.

Compounds of this invention can be used in combination with any one or more of antiviral agents, e.g. but not limited to those listed in Table A, and/or any one or more of LRAs, e.g. but not limited to, the LRAs described herein.

It is understood that the scope of combinations of the compounds of this invention with compatible anti-HIV agents is not limited to the HIV antivirals listed in Table A, but includes in principle any combination with any pharmaceutical composition useful for the treatment or prophylaxis of HIV AIDS, or ARC, with the exception of HIV protease inhibitors. The compatible HIV antiviral agents and other active agents will typically be employed in these combinations in their conventional dosage ranges and regimens as reported in the art, including, for example, the dosages described in the current Physicians' Desk Reference, Thomson PDR, 70th edition (2016), Montvale, NJ: PDR Network, or in prior editions thereof. The dosage ranges for a compound of the disclosure in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to the reverse transcriptase region within GAG-POL, e.g., by competitive inhibition.

Abbreviations and acronyms employed herein include the following: AcOH=Acetic acid; aq=aqueous; BisPin=bis(pinacolato)diboron; Boc=tert-butyloxycarbonyl; d=doublet; DCM=dichloromethane; DIPEA—diisopropylethylamine; dppf=1,1'-Bis(diphenylphosphino)ferrocene; DMA=dimethylacetamide; DMF=N,N-dimethylformamide; DMAP=4-dimethylaminopyridine; DME=dimethoxymethane; DMP=Dess-Martin periodinane; DMSO=dimethyl sulfoxide; Et=ethyl; EtOAc or EA=ethyl acetate; EtOH=ethanol; HIV=human immunodeficiency virus; HPLC=high performance liquid chromatography; hr or h=hour; L=liter; LDA=lithium diisopropylamide; m=multiplet; Me=methyl; MCCN=acetonitrile; MeOH=methanol; MHz=megahertz; min=minute; mL or ml=milliliters; mmol=millimoles; MS (ESI)=mass spectroscopy (electrospray ionization); NCS=N-chlorosuccinimide; NHS=normal human serum; NIS=N-iodosuccinimide; nBu=n-butyl; nM=nanomolar; NMR=nuclear magnetic resonance; PE=petroleum ether; Pin=pinacolato boronate ester; prep=preparative; RNA=ribonucleic acid; s=singlet; sat aq=saturated aqueous; sol=solution; t=triplet; TBAI=tetra-N-butylammonium iodide; TBAF=tetra-N-butylammonium fluoride; t-Bu=tert-butyl; THF=tetrahydrofuran; TFA=trifluoroacetic; TFAA=trifluoroacetic anhydride; TLC=thin layer chromatography; TMS=trimethylsilyl; and XPhos Pd G3=(2-Dicyclohexylphosphino-2',4',6'-triisopropyl-1,1'-biphenyl)[2-(2'-amino-1,1'-biphenyl)]palladium(II) methanesulfonate.

Methods for preparing the compounds of this invention are described in the following Schemes and Examples. Starting materials and intermediates are purchased or are made using known procedures, or as otherwise illustrated in the three Intermediate (A, B, and C) sections that follow. A frequently applied route to the compounds of Formula I are described in the Schemes that follow.

SCHEME 1

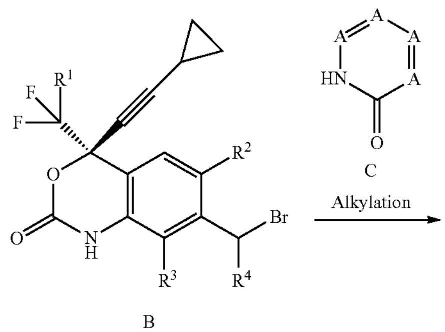

B

C

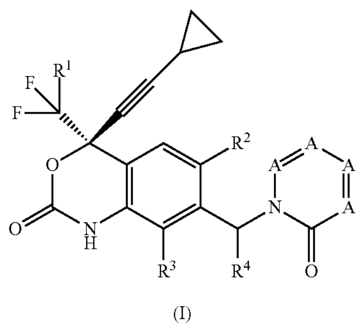

(I)

Scheme 1 depicts a method for preparing compounds of Formula I wherein $R^5$ is pyrimidinone and pyrazinone. Intermediate B is prepared with procedures illustrated in the Intermediate B section. The alkylation reaction using an appropriate 6-membered heterocyclic ring (Intermediate C) provides compounds of Formula I. Synthesis of C is illustrated in the Intermediate C section.

SCHEME 2

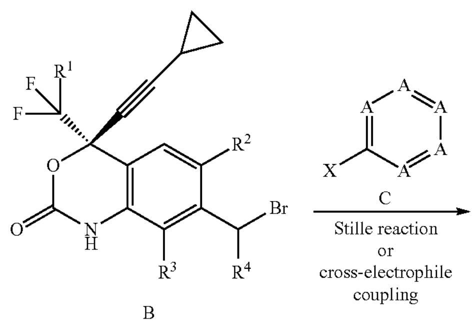

B

C

-continued

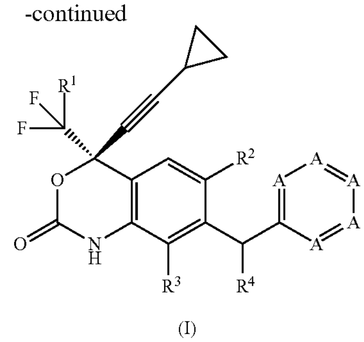

(I)

Scheme 2 depicts a method for preparing compounds of Formula I. Intermediate B is prepared with procedures illustrated in the Intermediate B section. An in situ Stille coupling or cross-electrophile mediated by Nickel using a phenyl ring or an appropriate 5 or 6-membered heterocyclic ring (Intermediate C) provides compounds of Formula I. Synthesis of C is illustrated in the Intermediate C section.

Reactions sensitive to moisture or air were performed under nitrogen or argon using anhydrous solvents and reagents. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure.

The progress of reactions was determined by either analytical thin layer chromatography (TLC) usually performed with E. Merck pre-coated TLC plates, silica gel 60F-254, layer thickness 0.25 mm or analytical liquid chromatography-mass spectrometry (LC-MS). Typically, the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min. LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 μm column using mobile phase containing A: 0.05% Trifluoroacetic acid in water and B: 0.05% Trifluoroacetic acid in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 μm column using mobile phase containing A: 0.05% Trifluoroacetic acid in water and B: 0.05% Trifluoroacetic acid in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 μm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 μm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. An alternate preparative HPLC system used was a Gilson Workstation consisting of: Gilson GX-281 Injector/Collector, Gilson UVNIS-155 Detector, Gilson 333 and 334 Pumps, and equipped with a column selected from the following: Phenomenexd Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM $NH_4HCO_3$ or 0.05% $NH_{40}H$) or low pH (0-95% acetonitrile/water eluent comprising 0.1% v/v TFA). The injection volume ranged from 1000-8000 μL, and the UV detection range was 210-400 nm. Mobile phase gradients were optimized for the individual compounds.

Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 μm, 60 Å pore size) in pre-packed cartridges of the size noted.

SFC chiral resolution was carried out on a Sepiate Prep SFC 100, Multigram II (MG II), THAR80 prep SFC, or a Waters SFC (80, 200, or 350).

Chiral preparative chromatography was conducted on one of CHIRALPAK AS, of CHIRALPAK AD, CHIRALCEL® OD, CHIRALCEL®IA, CHIRALCEL® OJ columns (20×250 mm) (Daicel Chemical Industries, Ltd.) or WHELK-O®1 (Regis Technologies, Inc.) with desired isocratic solvent systems identified on chiral analytical chromatography or by supercritical fluid (SFC) conditions.

Proton or $^1H$ NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker Avance III 500 MHz spectrometer equipped with a PABBO Probe 5 mm in accordance with standard analytical techniques, unless specified otherwise, and results of spectral analysis are reported. $^1H$ NMR spectra were acquired in $CDCl_3$ solutions unless otherwise noted. Chemical shifts were reported in parts per million (ppm). Tetramethylsilane (TMS) was used as internal reference in $CD_3Cl$ solutions, residual $CH_3OH$ peak or TMS was used as internal reference in $CD_3OD$ solutions, and TMS was used as internal reference in DMSO-d6 solutions. Coupling constants (J) were reported in hertz (Hz).

It is understood that a chiral center in a compound may exist in the "S" or "R" stereo-configuration, or as a mixture of both. Within a molecule, each bond drawn as a straight line from a chiral center encompasses each of the (R) and (S) stereoisomers as well as mixtures thereof unless otherwise noted. The (R) and (S) isomer mixtures in the Examples were separated, providing one or both of an isomer A (the faster eluting isomer) and an isomer B (the slower eluting isomer), based on their observed elution order resulting from the separation as performed in the Example. Elution time and/or order of separated isomers may differ if performed under conditions different than those employed herein. Absolute stereochemistry (R or S) of the chiral center in each of the "A" and/or "B" separated stereoisomers in the Examples was not determined, and "A" and "B" only refer to elution order resulting from the purification conditions as performed. An asterisk (*) may be used in the associated chemical structure drawings of the Intermediate and Example compounds to indicate a chiral center.

Compounds containing a bromine have two masses due to the two bromide isotopes, $^{79}Br$ and $^{81}Br$ in an approximately 1:1 ratio.

Intermediate A

Intermediate A01:4-(cyclopropylethynyl)-6-fluoro-7-(hydroxymethyl)-4-(trifluoromethyl)-1,4-dihydro-2H-benzo[d][1,3]oxazin-2-one

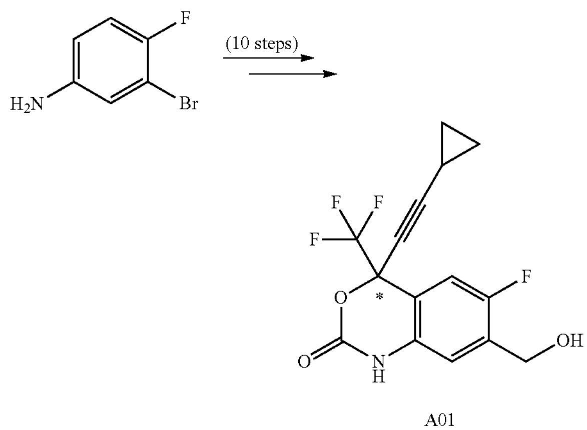

A01

Step 1: 5-bromo-4-fluoro-2-iodoaniline: To a solution of 3-bromo-4-fluoroaniline (25 g, 132 mmol) in AcOH (250 mL) was added NIS (32.6 g, 145 mmol). The mixture was stirred for 16 h at 26° C. The reaction mixture was concentrated and the resulting crude was poured into $H_2O$ (100 mL) and extracted with EtOAc (250 mL×3), washed with $H_2O$ (150 mL×3), sat aq $NaHCO_3$ solution (50 mL×2) and brine (100 mL), dried over $Na_2SO_4$, filtered and concentrated. The resulting residue was purified by column chromatography ($SiO_2$, 0-2% EtOAc:PE) to give the title compound.

Step 2: tert-butyl (5-bromo-4-fluoro-2-iodophenyl)(tert-butoxycarbonyl)carbamate: To a stirred solution of 5-bromo-4-fluoro-2-iodoaniline (14 g, 44.3 mmol) in DCM (80 mL) was added DMAP (0.271 g, 2.22 mmol). Then, di-tert-butyl dicarbonate (14.51 g, 66.5 mmol) was added.

The mixture was stirred at 26° C. for 4 h. The reaction mixture was concentrated and diluted with DCM (500 mL), washed with $H_2O$ (100 mL×2), brine (50 mL), dried over $Na_2SO_4$, filtered and concentrated to give the title compound, which was used as is.

Step 3: tert-butyl (5-bromo-4-fluoro-2-iodophenylcarbamate: To a stirred solution of tert-butyl (5-bromo-4-fluoro-2-iodophenyl)(tert-butoxycarbonyl)carbamate (20 g, 38.7 mmol) in MeOH (100 mL) was added $K_2CO_3$ (5.36 g, 38.7 mmol). The mixture was stirred at 26° C. for 14 h. The reaction mixture was concentrated and diluted with DCM (500 mL), washed with $H_2O$ (100 mL×2), brine (50 mL), dried over $Na_2SO_4$, filtered and concentrated to give the title compound, which was used as is.

Step 4: tert-butyl (5-bromo-4-fluoro-2-(2,2,2-trifluoroacetylphenylcarbamate: A mixture of tert-butyl (5-bromo-4-fluoro-2-iodophenyl)carbamate (12 g, 28.8 mmol) and ethyl 2,2,2-trifluoroacetate (16.39 g, 115 mmol) in THF (120 mL) was added a solution of isopropylmagnesium chloride-lithium chloride complex (55.5 mL, 72.1 mmol) in THF (35 mL) dropwise at −70° C. and stirred for 0.5 h. The reaction mixture was stirred at −70° C. for 1 h. The mixture was quenched with sat aq $NH_4Cl$ sol (100 mL) and $H_2O$ (100 mL), extracted with EtOAc (150 mL×2), washed with brine (150 mL), dried over $Na_2SO_4$, filtered, concentrated. The resulting residue was purified by prep-HPLC (water (10 mM $NH_4HCO_3$):MeCN) to give the title compound.

Step 5: tert-butyl (5-bromo-2-(4-cyclopropyl-1,1,1-trifluoro-2-hydroxy but-3-yn-2-yl)-4-fluorophenyl)carbamate: A stirred solution of tert-butyl (5-bromo-4-fluoro-2-(2,2,2-trifluoroacetyl)phenyl)carbamate (2 g, 5.18 mmol) in toluene (10 mL) was stirred at 130° C. for 16 h. In a separate flask, a solution of ethynylcyclopropane (1.712 g, 25.9 mmol) in toluene (2 mL) was treated with n-BuLi (11.91 ml, 11.91 mmol) at −60° C. and stirred for 0.5 h under $N_2$ at 25° C. To this mixture, it was added the above crude solution of tert-butyl (5-bromo-4-fluoro-2-(2,2,2-trifluoroacetyl)phenyl)carbamate (2 g, 5.18 mmol) in toluene dropwise at −60° C. The resulting mixture was allowed to stirred at 25° C. for 1 h. The reaction mixture was concentrated and the crude was poured into $H_2O$ (100 mL) and extracted with EtOAc (250 mL×3), washed with $H_2O$ (150 mL×3), sat aq $NaHCO_3$ sol (50 mL×2) and brine (100 mL), dried over $Na_2SO_4$, filtered and concentrated. The resulting crude was purified by column chromatography (0-20% EtOAc:PE) to give the title compound.

Step 6: tert-butyl (2-(4-cyclopropyl-1,1,1-trifluoro-2-hydroxybut-3-yn-2-yl)-4-fluoro-5-vinylphenyl)carbamate: To a solution of tert-butyl (5-bromo-2-(4-cyclopropyl-1,1,1-trifluoro-2-hydroxybut-3-yn-2-yl)-4-fluorophenyl)carbamate (1 g, 2.211 mmol) and potassium trifluoro(vinyl)borate (0.444 g, 3.32 mmol) in 1,4-dioxane (10 ml) and water (1 mL) was added $K_2CO_3$ (0.917 g, 6.63 mmol) and $PdC_2$ (dppf) (0.162 g, 0.22 mmol). Then, the reaction mixture was stirred at 80° C. for 6 h under $N_2$. The reaction was diluted with $H_2O$ (10 mL) and extracted with EtOAc (10 mL×3). The organic layer was washed with brine (10 mL), dried over anhydrous $Na_2SO_4$, filtered, concentrated to give the title compound, which was used as is.

Step 7: tert-butyl (2-(4-cyclopropyl-1,1,1-trifluoro-2-hydroxybut-3-yn-2-yl)-4-fluoro-5-formylphenyl)carbamate: To a stirred solution of tert-butyl (2-(4-cyclopropyl-1,1,1-trifluoro-2-hydroxybut-3-yn-2-yl)-4-fluoro-5-vinylphenyl) carbamate (800 mg, 2.00 mmol) in 1,4-dioxane (10 ml) and water (3 ml) was added 2,6-lutidine (429 mg, 4.01 mmol), osmium tetroxide (0.126 ml, 0.401 mmol), and then, sodium periodate (1285 mg, 6.01 mmol) at 0° C. The mixture was stirred for 10 min at 0° C., and then, at 25° C. for 6 h. The reaction was diluted in $H_2O$ (5 mL). The residue was extracted with EtOAc (5 mL×3). The organic layer was washed with brine (5 mL), dried over $Na_2SO_4$, filtered and concentrated to give the title compound.

Step 8: tert-butyl (2-(4-cyclopropyl-1,1,1-trifluoro-2-hydroxybut-3-yn-2-yl)-4-fluoro-5-(hydroxymethyl)phenyl) carbamate: To a stirred solution of tert-butyl (2-(4-cyclopropyl-1,1,1-trifluoro-2-hydroxybut-3-yn-2-yl)-4-fluoro-5-formylphenyl)carbamate (800 mg, 1.993 mmol) in MeOH (10 mL) was added $NaBH_4$ (37.7 mg, 0.997 mmol) at 0° C. The resulting mixture was stirred at 15° C. for 1 h. The reaction mixture was concentrated and the crude was diluted with $H_2O$ (50 mL) and extracted with EtOAc (50 mL×3), washed with $H_2O$ (50 mL×3), sat aq $NaHCO_3$ sol (50 mL×2) and brine (30 mL), dried over $Na_2SO_4$, filtered and concentrated. The resulting crude was purified by silica gel column chromatography (0-20% EtOAc:PE) to give the title compound.

Step 9: 2-(2-amino-5-fluoro-4-(hydroxymethyl)phenyl)-4-cyclopropyl-1,1,1-trifluorobut-3-yn-2-ol; A solution of tert-butyl (2-(4-cyclopropyl-1,1,1-trifluoro-2-hydroxybut-3-yn-2-yl)-4-fluoro-5-(hydroxymethyl)phenyl)carbamate (500 mg, 1.240 mmol) in 4M HCl/MeOH (4 mL) was stirred at 25° C. for 1 h. The solution was directly concentrated to dryness to give the title compound, which was used as is.

Step 10: 4-(cyclopropylethynyl)-6-fluoro-7-(hydroxymethyl)-4-(trifluoromethyl)-1,4-dihydro-2H-benzo[d][1,3] oxazin-2-one: A mixture of 2-(2-amino-5-fluoro-4-(hydroxymethyl)phenyl)-4-cyclopropyl-1,1,1-trifluorobut-3-yn-2-ol (400 mg, 1.319 mmol) and DIPEA (0.230 ml, 1.32 mmol) in THF (20 mL) was cooled to 0° C., triphosgene (196 mg, 0.660 mmol) in THF (1 mL) was dropwise to the mixture. The resulting mixture was stirred at 15° C. for 16 h. The mixture was quenched with sat aq $NaHCO_3$ sol (30 mL), extracted with EtOAc (20 mL×2). The combined organic layer was washed with brine (50 mL), dried with $Na_2SO_4$, filtered and concentrated. The resulting residue was purified by pre-TLC (60% EtOAc:PE) to give the title compound. MS (ESI) m/z 330.1 $[M+H]^+$.

Intermediate A02: 7-bromo-4-(cyclopropylethynyl)-4-(trifluoromethyl)-1H-benzo[d][1,3]oxazin-2(4H)-one

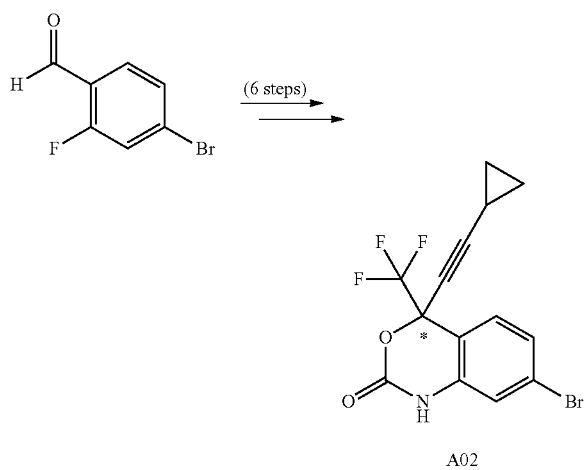

A02

Step 1: 1-(4-bromo-2-fluorophenyl)-2,2,2-trifluoroethanol: A solution of 4-bromo-2-fluorobenzaldehyde (15.0 g, 73.8 mmol) and $TMSCF_3$ (9.1 g, 66.4 mmol) in THF (90 mL) was added TBAF (1.2 mL) at 0° C. The mixture was stirred for 3 h at 20° C. Additional TBAF (14.8 mL) was added. The mixture was stirred for 10 min at 20° C. Aq 1M HCl (70 mL) was added and the mixture was stirred for 30 min. The mixture was diluted with $H_2O$ (100 mL) and extracted with EtOAc (100 mL×2), washed with brine (100 mL×2), dried over $Na_2SO_4$, and filtered and concentrated to give the title compound.

Step 2: 1-(4-bromo-2-fluorophenyl)-2,2,2-trifluoroethanone: A mixture of 1-(4-bromo-2-fluorophenyl)-2,2,2-trifluoroethanol (19.0 g, 69.5 mmol) and DMP (59.0 g, 139.1 mmol) and $NaHCO_3$ (23.3 g, 278.3 mmol) in DCM (200 mL) was stirred for 3 h at 20° C. The mixture was washed with aq $NaHCO_3$ (300 mL×2) and $H_2O$ (300 mL×2) and brine (200 mL) and dried over $Na_2SO_4$ and filtered and concentrated to give the title compound, which was used in the next step without further purification.

Step 3: 1-(4-bromo-2-((4-methoxybenzyl)amino)phenyl)-2,2,2-trifluoroethanone: A mixture of 1-(4-bromo-2-fluorophenyl)-2,2,2-trifluoroethanone (9.0 g, 33.2 mmol), $K_2CO_3$ (9.1 g, 66.4 mmol) and 4-methoxybenzylamine (9.1 g, 66.4 mmol) in toluene (90 mL) was stirred for 2 h at 120° C. The mixture was washed with 10% aq. citric acid (100 mL×2) and brine (100 mL) and dried over $Na_2SO_4$ and filtered and concentrated to give the title compound.

Step 4: 1-(2-amino-4-bromophenyl)-2,2,2-trifluoroethanone: A mixture of 1-(4-bromo-2-((4-methoxybenzyl)amino)phenyl)-2,2,2-trifluoroethanone (8.2 g, 21.1 mmol) and anisole (11.4 g, 105.6 mmol) in TFA (30 mL) was stirred at 20° C. for 1 h. The resulting reaction was quenched with water (100 mL), extracted with EtOAc (50 mL×2), washed with sat aq $NaHCO_3$ sol (100 mL×2) and brine (100 mL), dried over $Na_2SO_4$, and filtered and concentrated. The residue was purified by column chromatography ($SiO_2$, 5-15% EtOAc:PE) to give the title compound.

Step 5: 2-(2-amino-4-bromophenyl)-4-cyclopropyl-1,1,1-trifluorobut-3-yn-2-ol: A solution of cyclopropylacetylene (3.7 g, 57.0 mmol) in toluene (90 mL) was added $Et_2Zn$ (11.4 mL, 11.4 mmol) at 0° C. and the solution was stirred for 0.5 h at 0° C. n-BuLi (15.2 mL, 38.06 mmol) was added and the mixture was stirred for 2 h at 0° C. The resulting mixture was added dropwise to a solution of 1-(2-amino-4-bromophenyl)-2,2,2-trifluoroethanone (3.4 g, 12.69 mmol) in toluene (30 mL) at 0° C. The mixture was then stirred for 1 h at 0° C. The resulting reaction was quenched with 1M aq citric acid (160 mL) and the organic phase was separated and the aqueous layer was extracted with EtOAc (40 mL×2). The organic layers were combined and washed with brine (100 mL×2), dried over $Na_2SO_4$ and filtered and concentrated. The residue was purified by column chromatography ($SiO_2$, 5-15% EtOAc:PE) to give the title compound.

Step 6: 7-bromo-4-(cyclopropylethynyl)-4-(trifluoromethyl)-1H-benzo[d][1,3]oxazin-2(4H)-one. A mixture of 2-(2-amino-4-bromophenyl)-4-cyclopropyl-1,1,1-trifluorobut-3-yn-2-ol (0.84 g, 2.51 mmol) and CDI (2.04 g, 12.57 mmol) in THF (30 mL) was stirred at 55° C. for 6 h. The resulting mixture was concentrated and the resulting residue was diluted with water (50 mL) and extracted with EtOAc (50 mL×2), washed with brine (100 mL), dried over $Na_2SO_4$ and filtered and concentrated. The resulting residue was purified by column chromatography ($SiO_2$, 5-15% EtOAc:PE) to give the title compound. MS (ESI) m/z 360 $[M+H]^+$.

Intermediate A03: (S)-6-chloro-4-(cyclopropylethynyl)-7-(hydroxymethyl)-4-(trifluoromethyl)-1,4-dihydro-2H-benzo[d][1,3]oxazin-2-one AND (R)-6-chloro-4-(cyclopropylethynyl)-7-(hydroxymethyl)-4-(trifluoromethyl)-1,4-dihydro-2H-benzo[d][1,3]oxazin-2-one

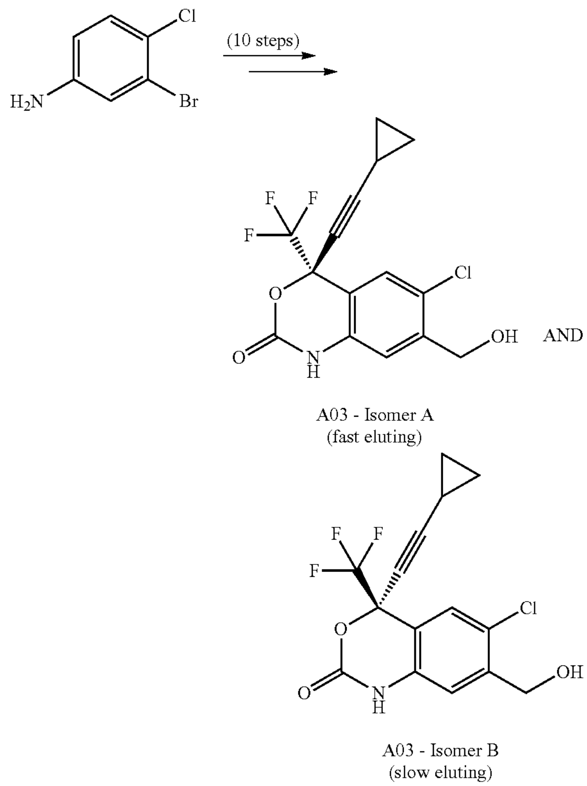

AND

A03 - Isomer A
(fast eluting)

A03 - Isomer B
(slow eluting)

Step 1: 5-bromo-4-chloro-2-iodoaniline: To a solution of 3-bromo-4-chloroaniline (50 g, 242 mmol) in AcOH (500 mL) was added NIS (46.3 g, 206 mmol) at 15° C. The mixture was stirred for 16 h at 15° C. The reaction mixture was concentrated and the resulting crude was poured into $H_2O$ (100 mL) and extracted with EA (250×3 mL), washed with $H_2O$ (150×3 mL), sat aq $NaHCO_3$ solution (50×2 mL) and brine (100 mL), dried over $Na_2SO_4$, filtered and concentrated. The resulting residue was purified by column chromatography ($SiO_2$, EA:PE=0%~2%) to give the title compound.

Step 2: tert-butyl (5-bromo-4-chloro-2-iodophenyl)(tert-butoxycarbonyl)carbamate. To a stirred solution of 5-bromo-4-chloro-2-iodoaniline (50 g, 150 mmol) in DCM (600 mL) was added di-tert-butyl dicarbonate (82 g, 376 mmol) and DMAP (1.838 g, 15.04 mmol). The reaction was stirred at 40° C. for 4 h. The reaction was concentrated and the residue was purified by column chromatography ($SiO_2$, PE:EA=1:0~95:5) to give the title compound.

Step 3: tert-butyl (5-bromo-4-chloro-2-iodophenyl)carbamate: To a stirred solution of tert-butyl (5-bromo-4-chloro-2-iodophenyl)(tert-butoxycarbonyl)carbamate (65 g, 122 mmol) in MeOH (100 mL) was added $K_2CO_3$ (135 g, 976 mmol). The mixture was stirred at 40° C. for 3 h. The reaction mixture was filtered and concentrated. The residue was dissolved in EA (100 mL), washed with $H_2O$ (100 mL), the organic layer was dried over ($Na_2SO_4$), filtered and concentrated. The resulting residue was washed with 30 mL (PE:EA=50:1) to give the title compound.

Step 4: tert-butyl (5-bromo-4-chloro-2-(2,2,2-trifluoroacetyl)phenyl)carbamate: A mixture of tert-butyl (5-bromo-4-chloro-2-iodophenyl)carbamate (30 g, 69.4 mmol) and ethyl 2,2,2-trifluoroacetate (39.4 g, 277 mmol) in THF (300 mL) was added a solution of isopropylmagnesium(II) lithium chloride (133 mL, 173 mmol) in THF (100 mL) dropwise at −70° C. and stirred for 1.5 h. The mixture was quenched with sat aq $NH_4Cl$ sol (200 mL) and $H_2O$ (200 mL), extracted with EA (200 mL×2), washed with brine (200 mL), dried over $Na_2SO_4$, filtered, concentrated and purified by column chromatography ($SiO_2$, PE:EA=5:1~5:2) to give the title compound.

Step 5: tert-butyl (5-bromo-4-chloro-2-(4-cyclopropyl-1,1,1-trifluoro-2-hydroxybut-3-yn-2-ylphenyl)carbamate. To a solution of ethynylcyclopropane (11.49 g, 174 mmol) in THF (500 mL) was added n-BuLi (32.0 ml, 80 mmol) dropwise at −70° C. and stirred for 0.5 h at 15° C. Then, a solution of tert-butyl (5-bromo-4-chloro-2-(2,2,2-trifluoroacetyl)phenyl)carbamate (14 g, 34.8 mmol) in toluene (200 mL) was stirred at 130° C. for 1 h, and then cooled down and added to the above solution at −70° C. The reaction mixture was stirred at 15° C. for 1 h. The mixture was quenched with sat aq $NH_4Cl$ sol (200 mL) and $H_2O$ (200 mL), extracted with EA (300 mL×2), washed with brine (300 mL), dried over $Na_2SO_4$, filtered, concentrated. The residue was purified by column chromatography ($SiO_2$, PE:EA=5:1~5:2) to give the title compound.

Step 6: tert-butyl (4-chloro-2-(4-cyclopropyl-1,1,1-trifluoro-2-hydroxybut-3-yn-2-yl)-5-vinylphenyl)carbamate. To a mixture of tert-butyl (5-bromo-4-chloro-2-(4-cyclopropyl-1,1,1-trifluoro-2-hydroxybut-3-yn-2-yl)phenyl)carbamate (10 g, 21.34 mmol) and potassium vinyltrifluoroborate (4.29 g, 32.0 mmol) in 1,4-dioxane (200 mL) and $H_2O$ (50 mL), were added $K_2CO_3$ (8.85 g, 64.0 mmol) and $PdC_2$ (dppf) (1.561 g, 2.134 mmol) under $N_2$. The reaction was stirred at 80° C. for 16 h. The reaction mixture was concentrated and purified by column chromatography ($SiO_2$, PE:EA=1:0~5:1) to give the title compound.

Step 7: tert-butyl (4-chloro-2-(4-cyclopropyl-1,1,1-trifluoro-2-hydroxybut-3-yn-2-yl)-5-formylphenyl)carbamate. To a mixture of tert-butyl (4-chloro-2-(4-cyclopropyl-1,1,1-trifluoro-2-hydroxybut-3-yn-2-yl)-5-vinylphenyl)carbamate (6 g, 14.43 mmol) and 2,6-dimethylpyridine (3.87 g, 36.1 mmol) in 1,4-dioxane (100 mL) and $H_2O$ (50 mL) was added a solution of osmium(VIII) oxide (0.367 g, 1.443 mmol) in t-BuOH (1 mL) dropwise. The reaction mixture was stirred at 15° C. for 5 min. Then, sodium periodate (10.80 g, 50.5 mmol) was added. The reaction was stirred at 15° C. for 1 h. The mixture was quenched with $Na_2S_2O_3$ (100 mL) and $H_2O$ (100 mL), extracted twice with EA (200 mL), and the combined organic layers were washed with brine (200 mL), dried over $Na_2SO_4$, filtered and concentrated to give the title compound, which was directly used in the next step.

Step 8: tert-butyl (4-chloro-2-(4-cyclopropyl-1,1,1-trifluoro-2-hydroxybut-3-yn-2-yl-5-(hydroxymethyl)phenyl) carbamate. To a mixture of tert-butyl (4-chloro-2-(4-cyclopropyl-1,1,1-trifluoro-2-hydroxybut-3-yn-2-yl)-5-formylphenyl)carbamate (6 g, 14.36 mmol) in MeOH (50 mL) was added $NaBH_4$ (0.109 g, 2.87 mmol). The reaction mixture was stirred at 15° C. for 1 h. The reaction was concentrated and purified by column chromatography ($SiO_2$, PE:EA=5:1~5:2) to give the title compound.

Step 9: 2-(2-amino-5-chloro-4-(hydroxymethyl)phenyl)-4-cyclopropyl-1,1,1-trifluorobut-3-yn-2-ol. A mixture of tert-butyl (4-chloro-2-(4-cyclopropyl-1,1,1-trifluoro-2-hydroxybut-3-yn-2-yl)-5-(hydroxymethyl)phenyl)carbamate (3 g, 7.15 mmol) in HCl/MeOH (30 mL) was stirred at 15° C. for 1 h. The mixture was quenched with sat aq $NaHCO_3$ sol (30 mL), extracted twice with EA (30 mL×2). The combined organic layer was washed with brine (30 mL), dried over $Na_2SO_4$, filtered and concentrated to give the title compound.

Step 10: (S)-6-chloro-4-(cyclopropylethynyl)-7-(hydroxymethyl)-4-(trifluoromethyl)-1,4-dihydro-2H-benzo[d][1,3]oxazin-2-one AND (R)-6-chloro-4-(cyclopropylethynyl)-7-(hydroxymethyl)-4-(trifluoromethyl-1,4-dihydro-2N-benzo[d][1,3]oxazin-2-one. A mixture of 2-(2-amino-5-chloro-4-(hydroxymethyl)phenyl)-4-cyclopropyl-1,1,1-trifluorobut-3-yn-2-ol (2.28 g, 7.13 mmol) and DIPEA (1.868 mL, 10.70 mmol) in THF (150 mL) was added triphosgene (0.846 g, 2.85 mmol) at 0° C. and stirred at 15° C. for 1 h. The reaction was concentrated and the resulting residue was purified by column chromatography ($SiO_2$, PE:EA=4:1~3:1) followed by SFC (DAICEL CHIRALPAK AD, 20% 0.1% $NH_3H_2O$:EtOH, 200 g/min): Isomer A (faster eluting): MS (ESI) m/z 346.0 $[M+H]^+$ AND Isomer B (slower eluting): MS (ESI) m/z 346.0 $[M+H]^+$ Intermediate A04: (S)-4-(cyclopropylethynyl)-4-(1,1-difluoroethyl)-7-(hydroxymethyl)-1,4-dihydro-2H-benzo[d][1,3]oxazin-2-one AND (R)-4-(cyclopropylethynyl)-4-(1,1-difluoroethyl)-7-(hydroxymethyl)-1,4-dihydro-2H-benzo[d][1,3]oxazin-2-one

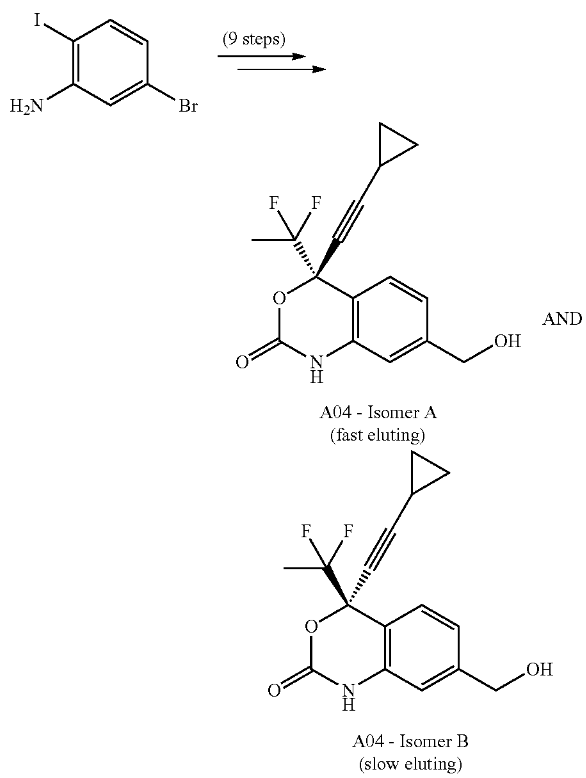

AND

A04 - Isomer A
(fast eluting)

A04 - Isomer B
(slow eluting)

Step 1: tert-butyl (5-bromo-2-iodophenyl)(tert-butoxycarbonyl)carbamate. To a stirred solution of 5-bromo-2-iodoaniline (5 g, 16.78 mmol) in DCM (50 mL) was added di-tert-butyl dicarbonate (9.16 g, 42.0 mmol) and DMAP (0.205 g, 1.678 mmol). The reaction was stirred at 40° C. for 4 h. The reaction was concentrated and purified by column chromatography ($SiO_2$, PE:EA=1:0~95:5) to give the title compound.

Step 2: tert-butyl (5-bromo-2-iodophenylcarbamate. To a stirred solution of tert-butyl (5-bromo-2-iodophenyl)(tert-butoxycarbonyl)carbamate (7 g, 14.05 mmol) in MeOH (80 mL) was added $K_2CO_3$ (9.71 g, 70.3 mmol). The mixture was stirred at 40° C. for 3 hour. The mixture was filtered and concentrated. The residue was dissolved in EA (100 mL), washed with $H_2O$ (100 mL), the organic layer was dried over ($Na_2SO_4$) and concentrated. The residue was washed with 30 mL (PE:EA=50:1) to give the title compound.

Step 3: tert-butyl (5-bromo-2-(2,2-difluoropropanoyl) phenyl)carbamate. A mixture of tert-butyl (5-bromo-2-iodophenyl)carbamate (3 g, 7.54 mmol) in THF (100 mL) was added 2,2-difluoro-N-methoxy-N-methylpropanamide (2.89 g, 18.84 mmol) dropwise at −70° C. and stirred for 0.5 h. Then, iPrMgCl (18.84 ml, 37.7 mmol) was added and the reaction mixture was stirred at −70° C. for 1 h. The reaction mixture was extracted with EA (50 mL×3) and the combined organic layer was concentrated and purified by column chromatography ($SiO_2$, PE:EA=1:0~95:5) to give the title compound.

Preparation of 2,2-difluoro-N-methoxy-N-methylpropanamide. To a solution of 2,2-difluoropropanoic acid (10 g, 91 mmol) in DCM (100 mL) was added $SOCl_2$ (6.96 mL, 95 mmol) at 0° C. under $N_2$. The reaction was stirred at 0° C. for 5 h. Then N,O-dimethylhydroxylamine hydrochloride (9.75 g, 100 mmol) and pyridine (25.7 mL, 318 mmol) was added at 0° C. The reaction was stirred at 15° C. for 16 h under $N_2$. Sat aq $NaHCO_3$ sol (100 mL) was added to the reaction and stirred at 15° C. for 0.5 h. The organic layer was separated and the aqueous layer was extracted with DCM (100 mL×3). The combined organic layer was washed with 2 M HCl (50 mL), sat aq $NaHCO_3$ (50 mL) and brine (50 mL), and then, was dried over ($Na_2SO_4$), filtered and concentrated to give the title compound.

Step 4: tert-butyl (5-bromo-2-(1-cyclopropyl-4,4-difluoro-3-hydroxypent-1-yn-3-yl)phenyl)carbamate. A solution of ethynylcyclopropane (1.361 g, 20.59 mmol) in THF (20 mL) was added nBuLi (3.79 ml, 9.47 mmol) dropwise at −70° C. and stirred for 0.5 h at 15° C. Then, a solution of tert-butyl (5-bromo-2-(2,2-difluoropropanoyl)phenyl)carbamate (1.5 g, 4.12 mmol) in toluene (4 mL) was added at −70° C. The reaction mixture was stirred at 15° C. for 1 h. The reaction was quenched with sat aq $NH_4Cl$ sol (20 mL) and $H_2O$ (20 mL) and extracted with EA (30 mL×2). The combined organic layer was washed with brine (30 mL), dried over $Na_2SO_4$, filtered, concentrated and purified by column chromatography ($SiO_2$, PE:EA=5:1~5:2) to give the title compound.

Step 5: tert-butyl (2-(1-cyclopropyl-4,4-difluoro-3-hydroxypent-1-yn-3-yl)-5-vinylphenyl)carbamate. To a mixture of tert-butyl (5-bromo-2-(1-cyclopropyl-4,4-difluoro-3-hydroxypent-1-yn-3-yl)phenyl)carbamate (1.8 g, 4.18 mmol) and potassium vinyltrifluoroborate (0.841 g, 6.27 mmol) in 1,4-dioxane (8 mL) and $H_2O$ (2 mL), were added $K_2CO_3$ (1.734 g, 12.55 mmol) and $PdC_2$(dppf) (0.306 g, 0.418 mmol). The reaction was stirred at 80° C. for 16 h. The reaction mixture was concentrated and purified by column chromatography ($SiO_2$, PE:EA=1:0~5:1) to give the title compound.

Step 6: tert-butyl (2-(1-cyclopropyl-4,4-difluoro-3-hydroxypent-1-yn-3-yl)-5-formylphenyl)carbamate. To a mixture of tert-butyl (2-(1-cyclopropyl-4,4-difluoro-3-hydroxypent-1-yn-3-yl)-5-vinylphenyl)carbamate (1.2 g, 3.18 mmol) and 2,6-dimethylpyridine (0.852 g, 7.95 mmol) in 1,4-dioxane (20 mL) and $H_2O$ (10 mL), were added a solution of osmium(VIII) oxide (0.081 g, 0.318 mmol) in t-BuOH (1 mL) dropwise. The reaction mixture was stirred at 15° C. for 5 min. Then, sodium periodate (2.380 g, 11.13 mmol) was added. The reaction was stirred at 15° C. for 1 h. The mixture was quenched with $Na_2S_2O_3$ (30 mL) and $H_2O$ (30 mL) and extracted with EA (50 mL×2). The combined organic layer was washed with brine (50 mL), dried over $Na_2SO_4$, filtered and concentrated to give the title compound.

Step 7: tert-butyl (2-(1-cyclopropyl-4,4-difluoro-3-hydroxypent-1-yn-3-yl)-5-(hydroxymethyl)phenyl)carbamate. A mixture of tert-butyl (2-(1-cyclopropyl-4,4-difluoro-3-hydroxypent-1-yn-3-yl)-5-formylphenyl)carbamate (1.2 g, 3.16 mmol) in MeOH (10 mL) was added $NaBH_4$ (0.024 g, 0.633 mmol). The reaction mixture was stirred at 15° C. for 1 h. The reaction was concentrated and purified by column chromatography ($SiO_2$, PE:EA=5:1~5:2) to give the title compound.

Step 8: 3-(2-amino-4-(hydroxymethylphenyl)-1-cyclopropyl-4,4-difluoropent-1-yn-3-ol. A mixture of tert-butyl (2-(1-cyclopropyl-4,4-difluoro-3-hydroxypent-1-yn-3-yl)-5-(hydroxymethyl)phenyl)carbamate (800 mg, 2.097 mmol) in HCl/MeOH (10 mL) was stirred at 40° C. for 1 h. The reaction was concentrated and the residue pH was adjusted with sat. aq. $NaHCO_3$ to pH=7 and then, extracted with EA (20 mL×3). The combined organic layer was concentrated to give the title compound.

Step 9: (S)-4-(cyclopropylethynyl)-4-(1,1-difluoroethyl)-7-(hydroxymethyl)-1,4-dihydro-2H-benzo[d][1,3]oxazin-2-one AND (R)-4-(cyclopropylethynyl)-4-(1,1-difluoroethyl)-7-hydroxymethyl-1,4-dihydro-2H-benzo[d][1,3]oxazin-2-one. A mixture of 3-(2-amino-4-(hydroxymethyl)phenyl)-1-cyclopropyl-4,4-difluoropent-1-yn-3-ol (500 mg, 1.777 mmol) and DIPEA (0.466 mL, 2.67 mmol) in THF (30 mL) was added triphosgene (211 mg, 0.711 mmol) at 0° C. and stirred at 15° C. for 1 h. The reaction was concentrated and the resulting residue was purified by column chromatography ($SiO_2$, PE:EA=4:1~3:1) followed by SFC (DAICEL CHIRALPAK AD, 30% 0.1% $NH_3H_2O$:EtOH, 65 g/min): Isomer A (faster eluting): MS (ESI) m/z 308.1 $[M+H]^+$ AND Isomer B (slower eluting): MS (ESI) m/z 308.1 $[M+H]^+$ Intermediate A05: (S) 6-chloro-4-(cyclopropylethynyl)-4-(1,1-difluoroethyl)-7-(hydroxymethyl)-1,4-dihydro-2H-benzo[d][1,3]oxazin-2-one AND (R) 6-chloro-4-(cyclopropylethynyl)-4-(1,1-difluoroethyl)-7-(hydroxymethyl)-1,4-dihydro-2H-benzo[d][1,3]oxazin-2-one

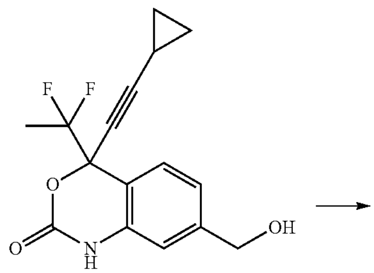

-continued

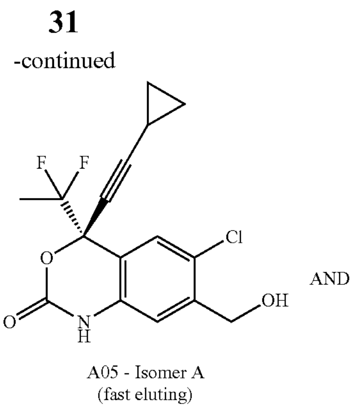

A05 - Isomer A
(fast eluting)

AND

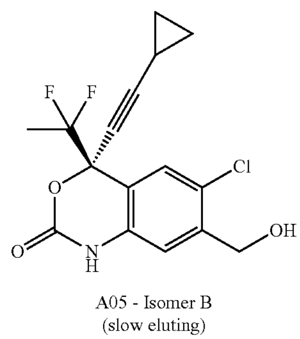

A05 - Isomer B
(slow eluting)

To a mixture of 4-(cyclopropylethynyl)-4-(1,1-difluoroethyl)-7-(hydroxymethyl)-1,4-dihydro-2H-benzo[d][1,3]oxazin-2-one (2 g, 6.51 mmol) in THF (100 mL) was added NCS (2 g, 14.98 mmol). The reaction was stirred at 40° C. for 2 h. The reaction was concentrated and the resulting residue was purified by pre-HPLC (MeCN:water with 0.1% TFA) followed by SFC (DAICEL CHIRALPAK AD, 27% 0.1% $NH_3H_2O$:EtOH, 55 g/min): Isomer A (faster eluting): MS (ESI) m/z 342.1 $[M+H]^+$ AND Isomer B (slower eluting): MS (ESI) m/z 342.1 $[M+H]^+$ Intermediate A06: (S)-4-(cyclopropylethynyl)-4-(1,1-difluoroethyl)-6-fluoro-7-(hydroxymethyl)-1,4-dihydro-2H-benzo[d][1,3]oxazin-2-one AND (R)-4-(cyclopropylethynyl)-4-(1,1-difluoroethyl)-6-fluoro-7-(hydroxymethyl)-1,4-dihydro-2H-benzo[d][1,3]oxazin-2-one

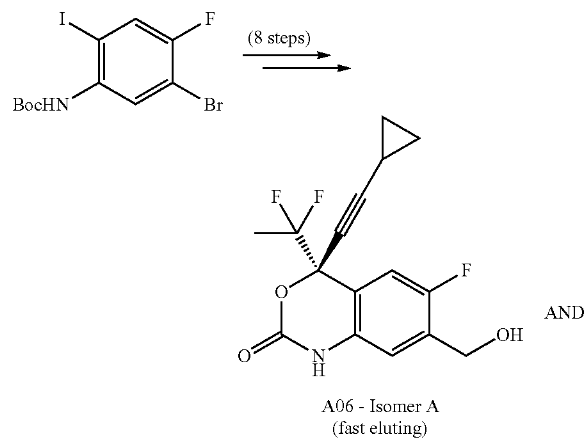

A06 - Isomer A
(fast eluting)

AND

-continued

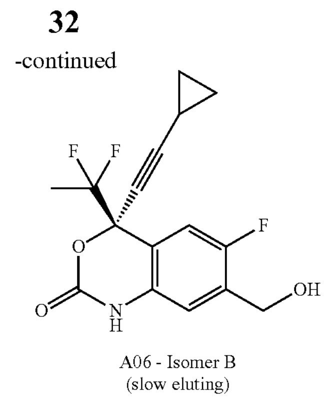

A06 - Isomer B
(slow eluting)

Step 1: tert-butyl (5-bromo-2-(2,2-difluoropropanoyl)-4-fluorophenyl)carbamate. A mixture of tert-butyl (5-bromo-4-fluoro-2-iodophenyl)carbamate (30 g, 72.1 mmol) and ethyl 2,2-difluoropropanoate (39.8 g, 288 mmol) in THF (300 mL) was added a solution of iPrMgCl·LiCl complex (139 mL, 180 mmol) in THF (30 mL) dropwise at −60° C. and stirred for 0.5 h. The reaction mixture was stirred at −60° C. for 1 h. The mixture was quenched with sat aq $NH_4Cl$ sol (200 mL) and $H_2O$ (200 mL) and extracted with EA (200 mL×2). The combined organic layer was washed with brine (500 mL), dried over $Na_2SO_4$, filtered and concentrated. The residue was purified by column chromatography ($SiO_2$, 100% PE) to give the title compound.

Step 2: tert-butyl (5-bromo-2-(1-cyclopropyl-4,4-difluoro-3-hydroxypent-1-yn-3-yl)-4-fluorophenylcarbamate. To a solution of ethynylcyclopropane (10.38 g, 157 mmol) in THF (120 mL) was added n-BuLi (72.2 mL, 72.2 mmol) at −60° C. and stirred for 0.5 h under $N_2$ at 25° C. Then, a solution of tert-butyl (5-bromo-2-(2,2-difluoropropanoyl)-4-fluorophenyl)carbamate (12 g, 31.4 mmol) in toluene (30 mL) was added at −60° C. The resulting mixture was stirred at 25° C. for 1 h. The reaction mixture was poured into sat aq $NH_4Cl$ sol (200 mL) and $H_2O$ (200 mL) and extracted with EA (200 mL×2). The combined organic layer was washed with brine (500 mL), dried over $Na_2SO_4$, filtered and concentrated. The residue was purified by column chromatography ($SiO_2$, 100% PE to 20% EA:PE) to give the title compound.

Step 3: tert-butyl (2-(1-cyclopropyl-4,4-difluoro-3-hydroxypent-1-yn-3-yl)-4-fluoro-5-formylphenyl)carbamate. To a solution of tert-butyl (5-bromo-2-(1-cyclopropyl-4,4-difluoro-3-hydroxypent-1-yn-3-yl)-4-fluorophenyl)carbamate (8 g, 17.85 mmol) in 1,4-dioxane (80 mL) and $H_2O$ (8 mL), were added $K_2CO_3$ (4.93 g, 35.7 mmol), potassium vinyltrifluoroborate (4.78 g, 35.7 mmol) and $PdCl_2$(dppf) (1.306 g, 1.785 mmol) under $N_2$ at 25° C. Then, the mixture was stirred at 80° C. for 16 h. $H_2O$ (50 mL) was added to the reaction and the mixture was extracted with EA (50 mL×3). The combined organic layers were washed with brine (20 mL), dried over $Na_2SO_4$, filtered and concentrated. The crude was purified by column chromatography ($SiO_2$, PE/EA=1:0~1:5) to give the title compound.

Step 4: tert-butyl (5-bromo-2-(2,2-difluoropropanoyl)-4-fluorophenylcarbamate. To a solution of tert-butyl (2-(1-cyclopropyl-4,4-difluoro-3-hydroxypent-1-yn-3-yl)-4-fluoro-5-vinylphenyl)carbamate (6 g, 15.17 mmol) in 1,4-dioxane (60 mL) and $H_2O$ (12 mL), were added 2,6-dimethylpyridine (4.06 g, 37.9 mmol) and osmium(VIII) oxide (0.386 g, 1.517 mmol) at 0° C. The reaction was stirred at 0° C. for 10 min. Then, sodium periodate (11.36 g, 53.1 mmol) was added. The reaction was stirred at 25° C. for 2 h. The reaction mixture was quenched with sat aq $Na_2SO_3$ sol (50 mL) and extracted with EA (50 mL×2). The combined organic layer was washed with brine (100 mL), dried over $Na_2SO_4$, filtered and concentrated to give the title compound, which was used for next step without further purification.

Step 5: tert-butyl (2-(1-cyclopropyl-4,4-difluoro-3-hydroxypent-1-yn-3-yl)-4-fluoro-5-(hydroxymethyl)phenyl) carbamate. To a solution of tert-butyl (2-(1-cyclopropyl-4,4-difluoro-3-hydroxypent-yn-3-yl)-4-fluoro-5-formylphenyl)carbamate (5 g, 12.58 mmol) in MeOH (40 mL) was added $NaBH_4$ (0.238 g, 6.29 mmol) at 0° C. The reaction was stirred at 25° C. for 10 min. $H_2O$ (100 mL) was added and the mixture was extracted with EA (100 mL×3). The combined organic layer was washed with brine (100 mL), dried over $Na_2SO_4$, filtered and concentrated. The crude was purified by column chromatography ($SiO_2$, PE/EA=1:0~1:5) to give the title compound.

Step 6: 3-(2-amino-5-fluoro-4-(hydroxymethyl)phenyl)-1-cyclopropyl-4,4-difluoropent-1-yn-3-91. A solution of tert-butyl (2-(1-cyclopropyl-4,4-difluoro-3-hydroxypent-1-yn-3-yl)-4-fluoro-5-(hydroxymethyl)phenyl)carbamate (4 g, 10.01 mmol) in 4M HCl/MeOH (40 mL) was stirred at 40° C. for 1 h. The mixture was concentrated and purified by column chromatography ($SiO_2$, PE/EA=1:0~1:2) to give the title compound.

Step 7: (S)-4-(cyclopropylethynyl)-4-(1,1-difluoroethyl)-6-fluoro-7-(hydroxymethyl)-1,4-dihydro-2H-benzo[d][1,3] oxazin-2-one AND (R)-4-(cyclopropylethynyl)-4-(1,1-difluoroethyl)-6-fluoro-7-(hydroxymethyl)-1,4-dihydro-2H-benzo[d][1,3]oxazin-2-one. A mixture of 3-(2-amino-5-fluoro-4-(hydroxymethyl)phenyl)-1-cyclopropyl-4,4-difluoropent-1-yn-3-ol (1.6 g, 5.35 mmol), DIPEA (1.401 ml, 8.02 mmol) in THF (50 mL) was cooled to 0° C., triphosgene (0.635 g, 2.138 mmol) in THF (2 mL) was drop-wise to the mixture and warmed to 25° C. and stirred for 1 h. The mixture was quenched with sat. aq. $NaHCO_3$ sol. (30 mL) and $H_2O$ (40 mL) The organic layer was separated and the aqueous layer was extracted with EA (30 mL×2). The combined organic layer was washed with brine (30 mL), dried over $Na_2SO_4$, filtered and concentrated. The residue was purified by column chromatography ($SiO_2$, PE/EA=1:0~1:2) followed by SFC (DAICEL CHIRALPAK AD, 35% 0.1% $NH_3H_2O$:EtOH, 62 mL/min): Isomer A (faster eluting): MS (ESI) m/z 326.4 $[M+H]^+$ AND Isomer B (slower eluting): MS (ESI) m/z 326.4 $[M+H]^+$ Intermediate B Intermediate B01:7-(bromomethyl-4-(cyclopropylethynyl)-6-fluoro-4-(trifluoromethyl-1,4-dihydro-2H-benzo[d][1,3]oxazin-2-one

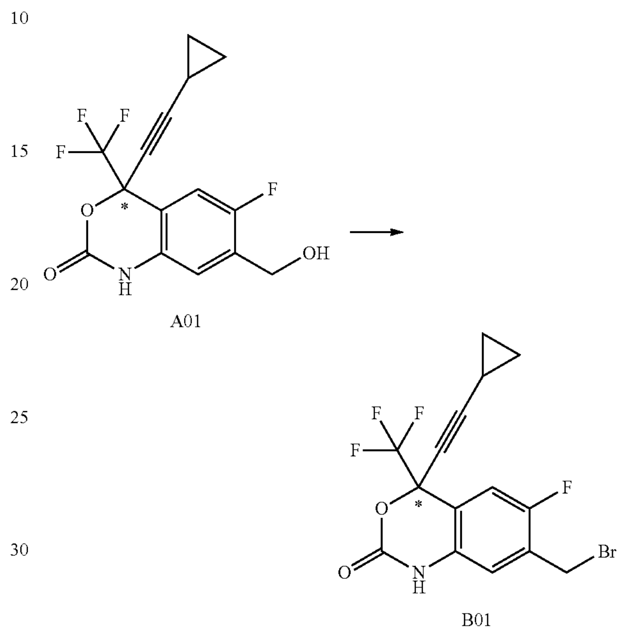
A01
B01

To a solution of intermediate A01 (310 mg, 0.942 mmol) and $CBr_4$ (468 mg, 1.41 mmol) in DCM (20 mL) was added triphenylphosphine (370 mg, 1.41 mmol) in DCM (1 mL) at 0° C. The resulting mixture was stirred at 25° C. for 1 h. The mixture was directly purified by pre-TLC ($SiO_2$, 50% EtOAc:PE) to give the title compound. MS (ESI) m/z 392.0/394.0 $[M+H]^+$.

The following intermediates were prepared using a procedure analogous to that used for making B01 using the noted starting intermediate in lace of A01.

| Intermediate |
| --- |
| B02 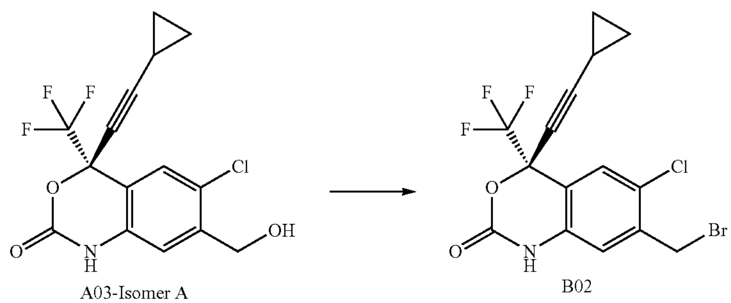 A03-Isomer A B02 |

-continued

| Intermediate |
|---|
| B03 |
| 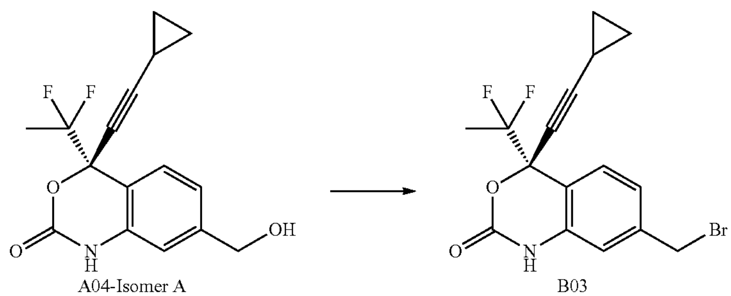 |
| A04-Isomer A B03 |
| B04 |
| 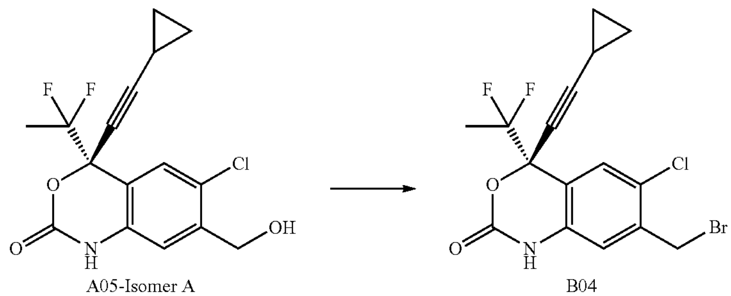 |
| A05-Isomer A B04 |
| B05 |
| 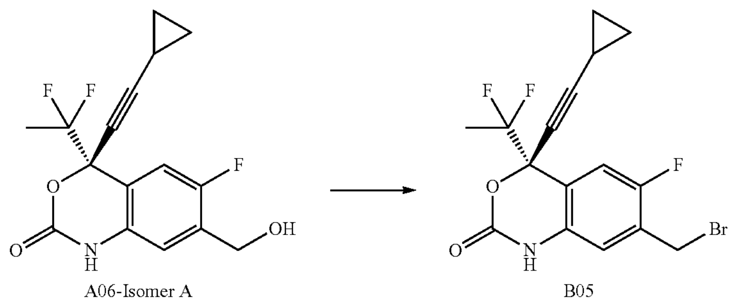 |
| A06-Isomer A B05 |

Intermediate C

Intermediate C01:2-amino-4-bromonicotinonitrile

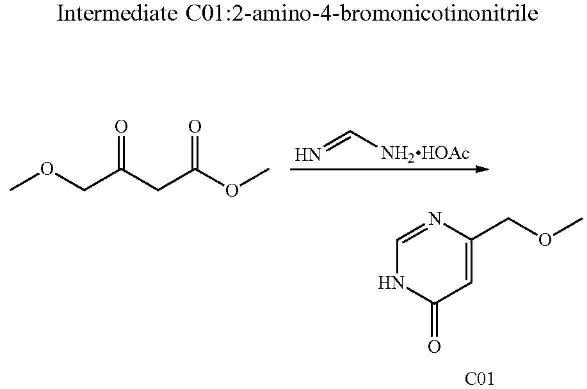

C01

To a solution of methyl 4-methoxy-3-oxobutanoate (8.71 g, 59.6 mmol) in MeOH (30 mL) was added formimidamide (2.5 g, 56.7 mmol) and sodium methoxide (3.22 g, 59.6 mmol) at 15° C. and stirred at 15° C. for 16 h. The reaction was concentrated and purified by pre-HPLC water (water with 10 mM $NH_4HCO_3$:MeCN) to give the title compound. MS (ESI) m/z 141.1 $[M+H]^+$.

Intermediate C02: 2-amino-4-bromonicotinonitrile

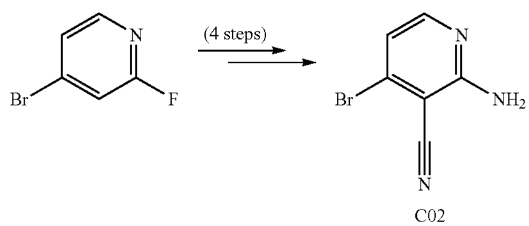

C02

Step 1: 4-bromo-2-fluoronicotinic acid: To a solution of 4-bromo-2-fluoropyridine (10 g, 56.8 mmol) in THF (120 ml) was added LDA (34.1 ml, 68.2 mmol) dropwise at −78° C. under $N_2$, and was stirred for 0.5 h at −78° C. The mixture was poured into $CO_2$ (100 g, 2272 mmol) and diluted with $H_2O$ (100 mL) and extracted with EtOAc (2×50 mL), the pH of the aq phase was adjusted with aq HCl (37%) to pH=6. The mixture was extracted with EtOAc (3×100 mL) and washed with brine (100 mL), dried over $Na_2SO_4$, filtered and concentrated to afford the title product.

Step 2: 4-bromo-2-fluoronicotinamide: The 4-bromo-2-fluoronicotinic acid (3.37 g, 15.32 mmol) was dissolved in 1,4-dioxane (30 mL) followed by the addition of pyridine (0.743 mL, 9.19 mmol), $Boc_2O$ (4.62 mL, 19.91 mmol) and ammonium bicarbonate (1.574 g, 19.91 mmol). The mixture was stirred at 15° C. for 12 h. The solution was concentrated and the crude was purified by prep-TLC ($SiO_2$, 50% EtOAc: PE) to afford the title compound.

Step 3: 4-bromo-2-fluoronicotinonitrile: To a solution of 4-bromo-2-fluoronicotinamide (2.27 g, 10.36 mmol) in THF (20 ml) was added TFAA (4.39 ml, 31.1 mmol) and $Et_3N$ (4.33 ml, 31.1 mmol). The reaction was stirred at 0° C. for 1 h. The mixture was poured into water (5 mL) and extracted with EtOAc (2×15 mL). The combined organic layer was washed with sat aq $NaHCO_3$ sol (15 mL), brine (15 mL) and dried over $Na_2SO_4$, filtered and concentrated. The residue was purified by column chromatography ($SiO_2$, 5-30% EtOAc/PE) to afford the title product.

Step 4: 2-amino-4-bromonicotinonitrile: To a solution of 4-bromo-2-fluoronicotinonitrile (200 mg, 0.995 mmol) in ammonia (1 ml) was stirred at 20° C. for 1 h. The solution was bubbled with $N_2$ to remove the ammonia, then extracted with EtOAc (2×5 mL). The combined organic layer was dried over $Na_2SO_4$, filtered and concentrated to afford the title product.

Intermediates used to prepare each of Examples 1-40 that were not commercially available were prepared as described above and are noted in the INT column in each of Tables 1-3.

Example 1: (S)-7-((3-amino-2-oxopyrazin-1(2H)-yl) methyl)-4-(cyclopropylethynyl)-6-fluoro-4-(trifluoromethyl)-1,4-dihydro-2H-benzo[d][1,3]oxazin-2-one AND (R)-7-((3-amino-2-oxopyrazin-1(2H)-yl) methyl)-4-(cyclopropylethynyl)-6-fluoro-4-(trifluoromethyl)-1,4-dihydro2H-benzo[d][1,3] oxazin-2-one

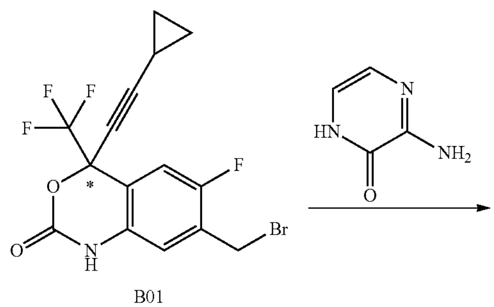

B01

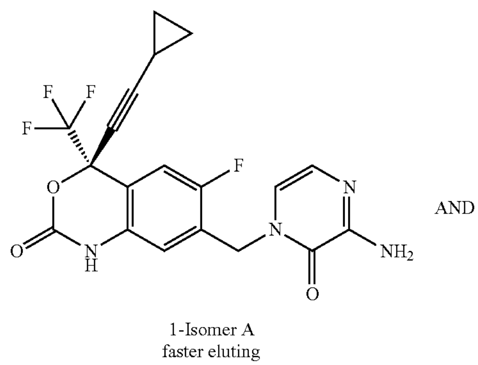

1-Isomer A
faster eluting

AND

-continued

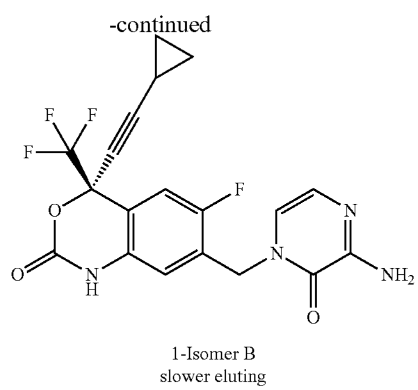

1-Isomer B
slower eluting

To a solution of intermediate B01 (40 mg, 0.102 mmol) and 3-aminopyrazin-2(1H)-one (11 mg, 0.102 mmol) in DMF (1 mL), was added $K_2CO_3$ (42.3 mg, 0.306 mmol). The mixture was stirred at 25° C. for 1 h. The mixture was quenched with $H_2O$ (10 mL), extracted with EtOAc (10 mL×2), washed with brine (10 mL), dried over $Na_2SO_4$, filtered and concentrated. The resulting residue was purified by prep-TLC (50% EtOAc:PE) followed by SFC (DAICEL CHIRALPAK AD, 46% 0.1% $NH_3H_2O$:EtOH, 75 ml/min): Isomer A (faster eluting): $^1$H NMR (400 MHz, MeCN-$d_3$) δ 8.43 (br s, 1H), 7.34-7.32 (d, J=9.6 Hz, 1H), 6.76-6.70 (m, 3H), 5.73 (br s, 2H), 5.09-4.99 (m, 2H), 1.47-1.40 (m, 1H), 0.95-0.89 (m, 2H), 0.82-0.79 (m, 2H). MS (ESI) m/z 423.1 $[M+H]^+$ AND Isomer B (slower eluting): $^1$H NMR (400 MHz, MeCN-$d_3$) δ 8.45 (br s, 1H), 7.35-7.32 (d, J=9.6 Hz, 1H), 6.78-6.71 (m, 3H), 5.94 (br s, 2H), 5.08-5.00 (m, 2H), 1.47-1.45 (m, 1H), 0.95-0.90 (m, 2H), 0.82-0.79 (m, 2H). MS (ESI) m/z 423.1 $[M+H]^+$ Example 2: (S)-4-(cyclopropylethynyl)-6-fluoro-7-((6-oxopyrimidin-1(6H)-yl)methyl)-4-(trifluoromethyl)-1,4-dihydro-2H-benzo[d][1,3]oxazin-2-one AND (R)-4-(cyclopropylethynyl-6-fluoro-7-((6-oxopyrimidin-1(6H-yl)methyl)-4-(trifluoromethyl)-1,4-dihydro-2H-benzo[d][1,3]oxazin-2-one

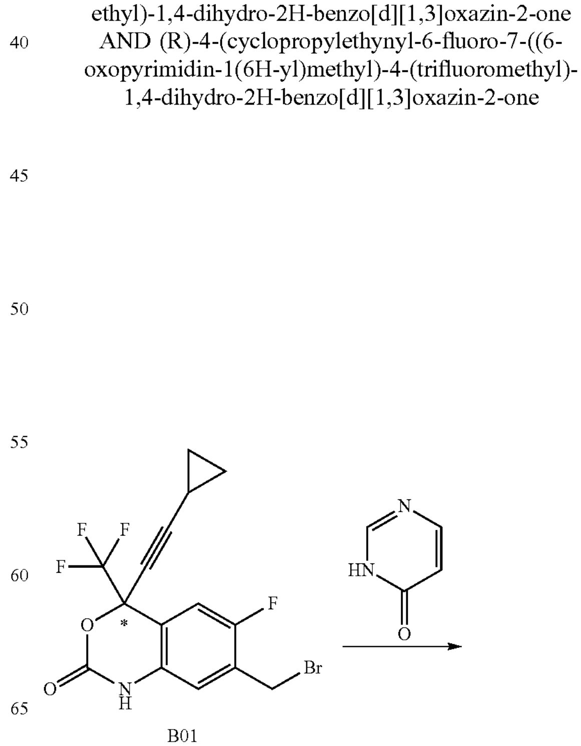

B01

-continued

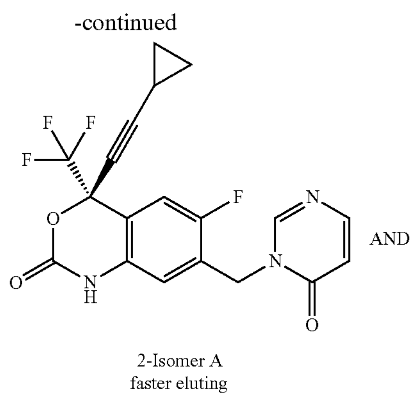

AND

2-Isomer A
faster eluting

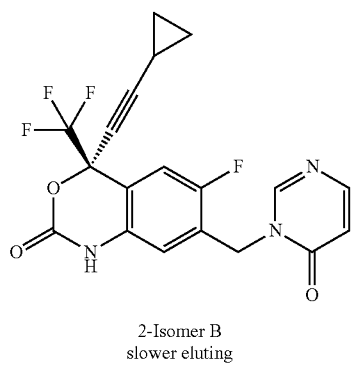

2-Isomer B
slower eluting

To a solution of intermediate B01 (40 mg, 0.102 mmol) and pyrimidin-4(3H)-one (19.60 mg, 0.204 mmol) in DMF (1 mL), was added $K_2CO_3$ (42.3 mg, 0.306 mmol). The mixture was stirred at 20° C. for 1 h. The mixture was quenched with $H_2O$ (10 mL), extracted with EtOAc (10 mL×2), washed with brine (10 mL), dried over $Na_2SO_4$, filtered and concentrated. The resulting residue was purified by prep-HPLC (water:MeCN with 0.1% TFA) followed by SFC (DAICEL CHIRALPAK AD, 33% 0.1% $NH_3H_2O$: MeOH, 60 ml/min): Isomer A (faster eluting): $^1$H NMR (400 MHz, MCCN-$d_3$) δ 8.30 (s, 1H), 7.90-7.89 (d, J=6.6 Hz, 1H), 7.35-7.32 (d, J=9.7 Hz, 1H), 6.87-6.86 (d, J=6.1 Hz, 1H), 6.40-6.39 (d, J=6.6 Hz, 1H), 5.08 (s, 2H), 1.46-1.43 (m, 1H), 0.93-0.90 (m, 2H), 0.81-0.80 (m, 2H). MS (ESI) m/z 408.1 $[M+H]^+$ AND Isomer B (slower eluting): $^1$H NMR (400 MHz, MCCN-$d_3$) δ 8.30 (s, 1H), 7.90-7.89 (d, J=6.6 Hz, 1H), 7.35-7.32 (d, J=9.9 Hz, 1H), 6.87-6.86 (d, J=6.1 Hz, 1H), 6.40-6.39 (d, J=6.6 Hz, 1H), 5.08 (s, 2H), 1.48-1.46 (m, 1H), 0.93-0.90 (m, 2H), 0.81-0.80 (m, 2H). MS (ESI) m/z 408.1 $[M+H]^+$.

Example 3: (S)-7-((5-amino-6-oxopyrimidin-1(6H)-ylmethyl)-4-(cyclopropylethynyl)-6-fluoro-4-(trifluoromethyl)-1,4-dihydro-2H-benzo[d][1,3]oxazin-2-one AND (R)-7-((5-amino-6-oxopyrimidin-1(6H)-ylmethyl)-4-(cyclopropylethynyl)-6-fluoro-4-(trifluoromethyl)-1,4-dihydro-2H-benzo[d][1,3]oxazin-2-one

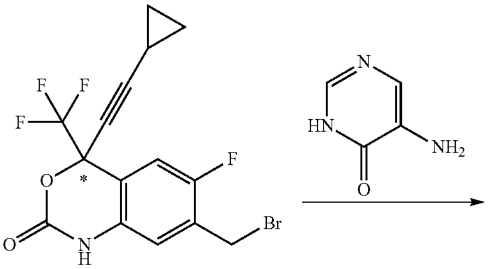

B01

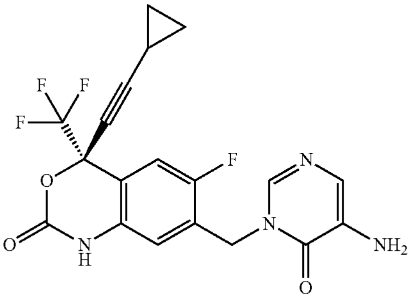

AND

3-Isomer A
faster eluting

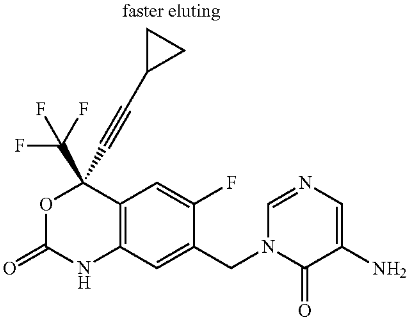

3-Isomer B
slower eluting

To a solution of intermediate B01 (30 mg, 0.077 mmol) and 5-aminopyrimidin-4(3H)-one (17.00 mg, 0.153 mmol) in DMF (2 mL), were added $K_2CO_3$ (31.7 mg, 0.230 mmol) and KI (12.70 mg, 0.077 mmol). The mixture was stirred at 25° C. for 4 h. The mixture was quenched with $H_2O$ (10 mL), extracted with EtOAc (10 mL×2), washed with brine (10 mL), dried over $Na_2SO_4$, filtered and concentrated. The resulting residue was purified by pre-HPLC (water:MeCN with 0.1% TFA) followed by SFC (DAICEL CHIRALPAK AD, 15% (0.1% $NH_3H_2O$):EtOH): Isomer A (faster eluting): $^1$H NMR (400 MHz, MeCN-$d_3$) δ 8.56 (br s, 1H), 8.16 (br s, 1H), 7.34 (br d, J=9.6 Hz, 2H), 6.89 (br d, J=6.1 Hz, 1H), 5.15 (s, 2H), 1.47-1.41 (m, 1H), 0.94-0.90 (m, 2H), 0.87-0.72 (m, 2H). MS (ESI) m/z 423.1 $[M+H]^+$ AND Isomer B (slower eluting): $^1$H NMR (400 MHz, MeCN-$d_3$) δ 8.49 (br s, 1H), 8.06 (br s, 1H), 7.36-7.30 (m, 2H), 6.87 (d, J=6.1 Hz, 1H), 5.14 (m, 2H), 1.46-1.41 (m, 1H), 0.95-0.90 (m, 2H), 0.82-0.79 (m, 2H). MS (ESI) m/z 423.1 $[M+H]^+$ The compounds in Table 1 were prepared in an analogous fashion to that described for Example 1 and separated by SFC (DAICEL CHIRALPAK AD, 15-30% (0.1% $NH_3H_2O$):EtOH) when required. "INT" is an abbreviation for intermediate. .

TABLE 1

| Ex. | Structure | IUPAC Name | MS [M + 1] | INT |
|---|---|---|---|---|
| 4 | 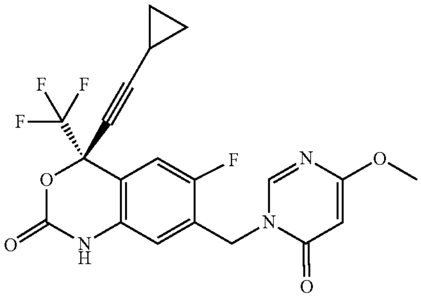 [SMILES: COc1cc(=O)n(Cc2cc3c(cc2F)[C@@](C#CC2CC2)(C(F)(F)F)OC(=O)N3)cn1] isomer A (Faster eluting) | (S)-4-(cyclopropylethynyl)-6-fluoro-7-((4-methoxy-6-oxopyrimidin-1(6H)-yl)methyl)-4-(trifluoromethyl)-1,4-dihydro-2H-benzo[d][1,3]oxazin-2-one | 438.1 | B01 |
| 5 | 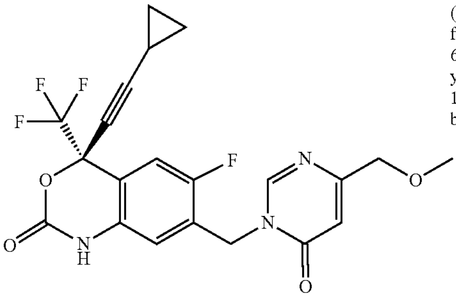 isomer A (Faster eluting) | (S)-4-(cyclopropylethynyl)-6-fluoro-7-((4-(methoxymethyl)-6-oxopyrimidin-1(6H)-yl)methyl)-4-(trifluoromethyl)-1,4-dihydro-2H-benzo[d][1,3]oxazin-2-one | 452.1 | B01/C01 |
| 6 | 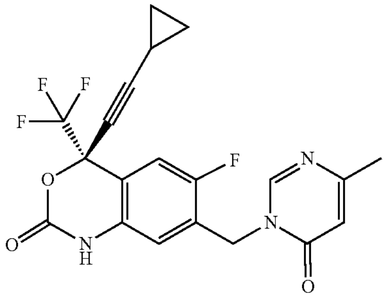 [SMILES: Cc1cc(=O)n(Cc2cc3c(cc2F)[C@@](C#CC2CC2)(C(F)(F)F)OC(=O)N3)cn1] isomer A (Faster eluting) | (S)-4-(cyclopropylethynyl)-6-fluoro-7-((4-methyl-6-oxopyrimidin-1(6H)-yl)methyl)-4-(trifluoromethyl)-1,4-dihydro-2H-benzo[d][1,3]oxazin-2-one | 422.1 | B01 |
| 7 | 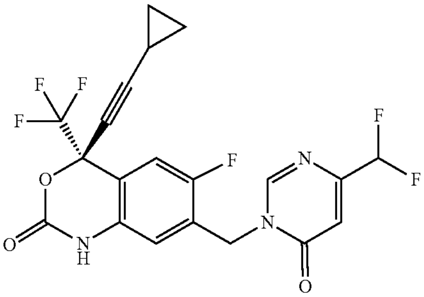 [SMILES: O=C1Nc2cc(Cn3cnc(C(F)F)cc3=O)c(F)cc2[C@@](C#CC2CC2)(C(F)(F)F)O1] isomer A (Faster eluting) | (S)-4-(cyclopropylethynyl)-7-((4-(difluoromethyl)-6-oxopyrimidin-1(6H)-yl)methyl)-6-fluoro-4-(trifluoromethyl)-1,4-dihydro-2H-benzo[d][1,3]oxazin-2-one | 458.0 | B01 |

TABLE 1-continued

| Ex. | Structure | IUPAC Name | MS [M + 1] | INT |
|---|---|---|---|---|
| 8 | 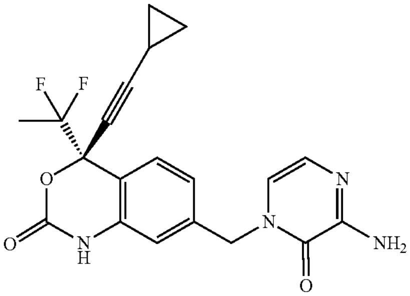 [SMILES: CC(F)(F)[C@@]1(C#CC2CC2)OC(=O)Nc2cc(Cn3ccnc(N)c3=O)ccc21] | (S)-7-((3-amino-2-oxopyrazin-1(2H)-yl)methyl)-4-(cyclopropylethynyl)-4-(1,1-difluoroethyl)-1,4-dihydro-2H-benzo[d][1,3]oxazin-2-one | 401.2 | B03 |
| 9 | 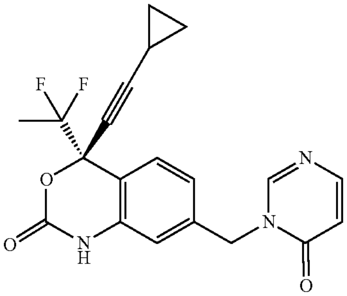 [SMILES: CC(F)(F)[C@@]1(C#CC2CC2)OC(=O)Nc2cc(Cn3cnccc3=O)ccc21] | (S)-4-(cyclopropylethynyl)-4-(1,1-difluoroethyl)-7-((6-oxopyrimidin-1(6H)-yl)methyl)-1,4-dihydro-2H-benzo[d][1,3]oxazin-2-one | 386.1 | B03 |
| 10 | 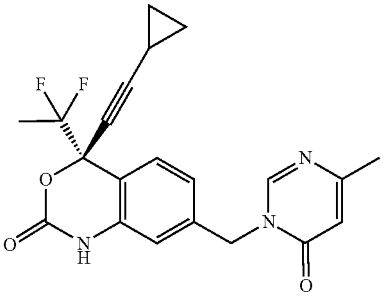 [SMILES: Cc1cc(=O)n(Cc2ccc3c(c2)NC(=O)O[C@]3(C#CC2CC2)C(C)(F)F)cn1] | (S)-4-(cyclopropylethynyl)-4-(1,1-difluoroethyl)-7-((4-methyl-6-oxopyrimidin-1(6H)-yl)methyl)-1,4-dihydro-2H-benzo[d][1,3]oxazin-2-one | 400.2 | B03 |
| 11 | 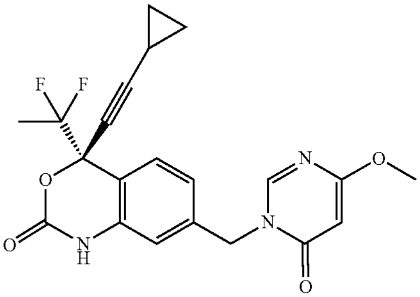 [SMILES: COc1cc(=O)n(Cc2ccc3c(c2)NC(=O)O[C@]3(C#CC2CC2)C(C)(F)F)cn1] | (S)-4-(cyclopropylethynyl)-4-(1,1-difluoroethyl)-7-((4-methoxy-6-oxopyrimidin-1(6H)-yl)methyl)-1,4-dihydro-2H-benzo[d][1,3]oxazin-2-one | 416.2 | B03 |
| 12 | 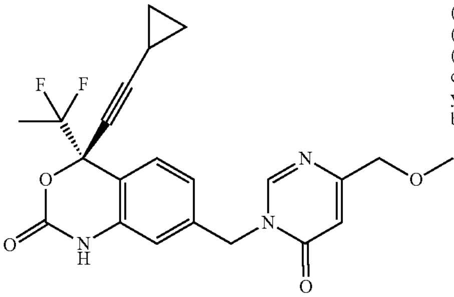 [SMILES: COCc1cc(=O)n(Cc2ccc3c(c2)NC(=O)O[C@]3(C#CC2CC2)C(C)(F)F)cn1] | (S)-4-(cyclopropylethynyl)-4-(1,1-difluoroethyl)-7-((4-(methoxymethyl)-6-oxopyrimidin-1(6H)-yl)methyl)-1,4-dihydro-2H-benzo[d][1,3]oxazin-2-one | 430.2 | B03/C01 |

TABLE 1-continued

| Ex. | Structure | IUPAC Name | MS [M + 1] | INT |
|---|---|---|---|---|
| 13 | 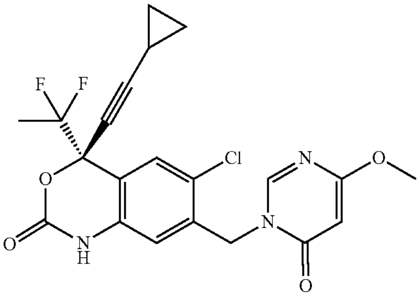 [SMILES: COc1cc(=O)n(Cc2cc3c(cc2Cl)[C@@](C#CC2CC2)(C(C)(F)F)OC(=O)N3)cn1] | (S)-6-chloro-4-(cyclopropylethynyl)-4-(1,1-difluoroethyl)-7-((4-methoxy-6-oxopyrimidin-1(6H)-yl)methyl)-1,4-dihydro-2H-benzo[d][1,3]oxazin-2-one | 450.1 | B04 |
| 14 | 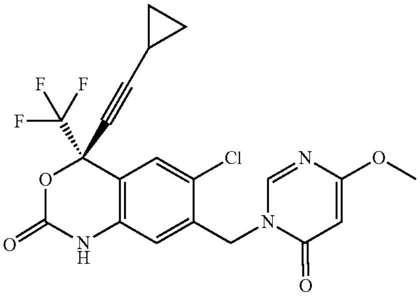 [SMILES: COc1cc(=O)n(Cc2cc3c(cc2Cl)[C@@](C#CC2CC2)(C(F)(F)F)OC(=O)N3)cn1] | (S)-6-chloro-4-(cyclopropylethynyl)-7-((4-methoxy-6-oxopyrimidin-1(6H)-yl)methyl)-4-(trifluoromethyl)-1,4-dihydro-2H-benzo[d][1,3]oxazin-2-one | 454.1 | B02 |
| 15 | 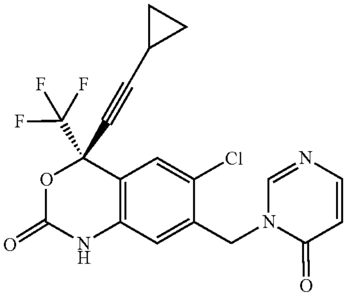 [SMILES: O=C1Nc2cc(Cn3cnccc3=O)c(Cl)cc2[C@@](C#CC2CC2)(C(F)(F)F)O1] | (S)-6-chloro-4-(cyclopropylethynyl)-7-((6-oxopyrimidin-1(6H)-yl)methyl)-4-(trifluoromethyl)-1,4-dihydro-2H-benzo[d][1,3]oxazin-2-one | 424.0 | B02 |
| 16 | 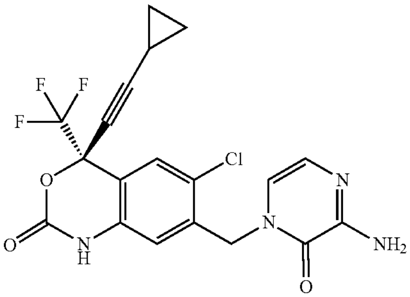 [SMILES: Nc1nccn(Cc2cc3c(cc2Cl)[C@@](C#CC2CC2)(C(F)(F)F)OC(=O)N3)c1=O] | (S)-7-((3-amino-2-oxopyrazin-1(2H)-yl)methyl)-6-chloro-4-(cyclopropylethynyl)-4-(trifluoromethyl)-1,4-dihydro-2H-benzo[d][1,3]oxazin-2-one | 439.1 | B02 |
| 17 | 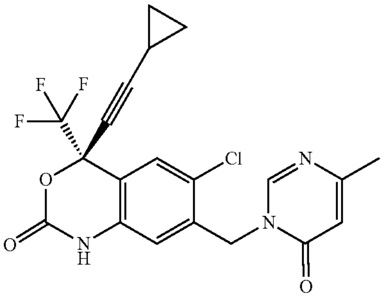 [SMILES: Cc1cc(=O)n(Cc2cc3c(cc2Cl)[C@@](C#CC2CC2)(C(F)(F)F)OC(=O)N3)cn1] | (S)-6-chloro-4-(cyclopropylethynyl)-7-((4-methyl-6-oxopyrimidin-1(6H)-yl)methyl)-4-(trifluoromethyl)-1,4-dihydro-2H-benzo[d][1,3]oxazin-2-one | 437.8 | B02 |

TABLE 1-continued

| Ex. | Structure | IUPAC Name | MS [M + 1] | INT |
|---|---|---|---|---|
| 18 | 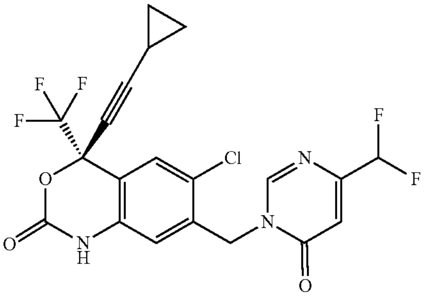 [SMILES: O=C1Nc2cc(Cn3cnc(C(F)F)cc3=O)c(Cl)cc2[C@@](C#CC2CC2)(C(F)(F)F)O1] | (S)-6-chloro-4-(cyclopropylethynyl)-7-((4-(difluoromethyl)-6-oxopyrimidin-1(6H)-yl)methyl)-4-(trifluoromethyl)-1,4-dihydro-2H-benzo[d][1,3]oxazin-2-one | 474.0 | B02 |
| 19 | 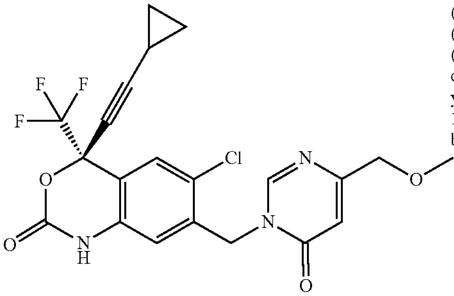 [SMILES: COCc1cc(=O)n(Cc2cc3c(cc2Cl)[C@@](C#CC2CC2)(C(F)(F)F)OC(=O)N3)cn1] | (S)-6-chloro-4-(cyclopropylethynyl)-7-((4-(methoxymethyl)-6-oxopyrimidin-1(6H)-yl)methyl)-4-(trifluoromethyl)-1,4-dihydro-2H-benzo[d][1,3]oxazin-2-one | 468.1 | B02 |
| 20 | 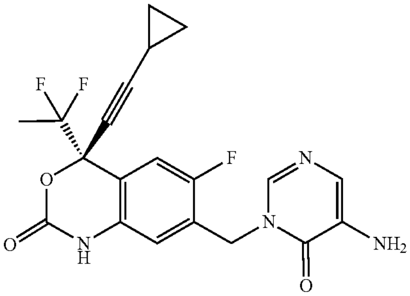 [SMILES: CC(F)(F)[C@@]1(C#CC2CC2)OC(=O)Nc2cc(Cn3cncc(N)c3=O)c(F)cc21] | (S)-7-((5-amino-6-oxopyrimidin-1(6H)-yl)methyl)-4-(cyclopropylethynyl)-4-(1,1-difluoroethyl)-6-fluoro-1,4-dihydro-2H-benzo[d][1,3]oxazin-2-one | 418.8 | B05 |
| 21 | 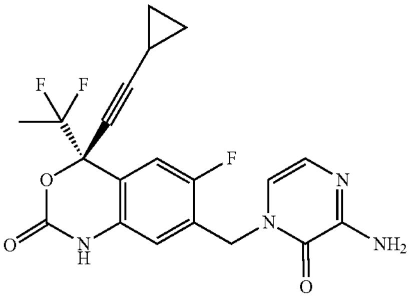 [SMILES: CC(F)(F)[C@@]1(C#CC2CC2)OC(=O)Nc2cc(Cn3ccnc(N)c3=O)c(F)cc21] | (S)-7-((3-amino-2-oxopyrazin-1(2H)-yl)methyl)-4-(cyclopropylethynyl)-4-(1,1-difluoroethyl)-6-fluoro-1,4-dihydro-2H-benzo[d][1,3]oxazin-2-one | 419.1 | B05 |
| 22 | 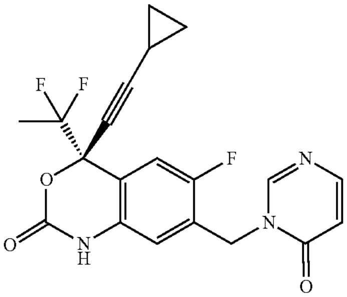 [SMILES: CC(F)(F)[C@@]1(C#CC2CC2)OC(=O)Nc2cc(Cn3cnccc3=O)c(F)cc21] | (S)-4-(cyclopropylethynyl)-4-(1,1-difluoroethyl)-6-fluoro-7-((6-oxopyrimidin-1(6H)-yl)methyl)-1,4-dihydro-2H-benzo[d][1,3]oxazin-2-one | 404.1 | B05 |

TABLE 1-continued

| Ex. | Structure | IUPAC Name | MS [M + 1] | INT |
|---|---|---|---|---|
| 23 | 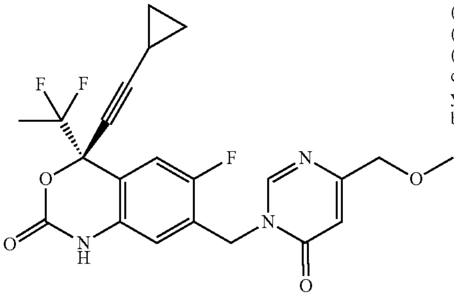 [SMILES: COCc1cc(=O)n(Cc2cc3c(cc2F)[C@@](C#CC2CC2)(C(C)(F)F)OC(=O)N3)cn1] | (S)-4-(cyclopropylethynyl)-4-(1,1-difluoroethyl)-6-fluoro-7-((4-(methoxymethyl)-6-oxopyrimidin-1(6H)-yl)methyl)-1,4-dihydro-2H-benzo[d][1,3]oxazin-2-one | 448.1 | B05 |
| 24 | 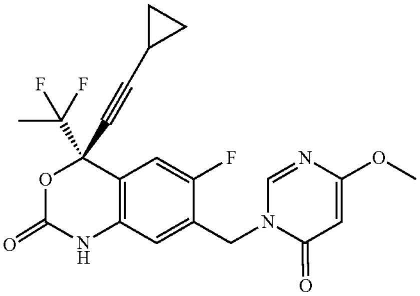 [SMILES: COc1cc(=O)n(Cc2cc3c(cc2F)[C@@](C#CC2CC2)(C(C)(F)F)OC(=O)N3)cn1] | (S)-4-(cyclopropylethynyl)-4-(1,1-difluoroethyl)-6-fluoro-7-((4-methoxy-6-oxopyrimidin-1(6H)-yl)methyl)-1,4-dihydro-2H-benzo[d][1,3]oxazin-2-one | 434.4 | B05 |
| 25 | 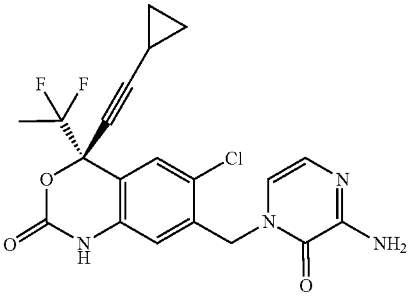 [SMILES: CC(F)(F)[C@@]1(C#CC2CC2)OC(=O)Nc2cc(Cn3ccnc(N)c3=O)c(Cl)cc21] | (S)-7-((3-amino-2-oxopyrazin-1(2H)-yl)methyl)-6-chloro-4-(cyclopropylethynyl)-4-(1,1-difluoroethyl)-1,4-dihydro-2H-benzo[d][1,3]oxazin-2-one | 435.2 | B04 |
| 26 | 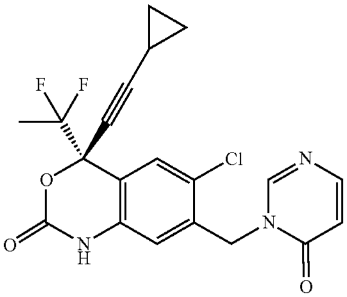 | (S)-6-chloro-4-(cyclopropylethynyl)-4-(1,1-difluoroethyl)-7-((6-oxopyrimidin-1(6H)-yl)methyl)-1,4-dihydro-2H-benzo[d][1,3]oxazin-2-one | 420.1 | B04 |
| 27 | 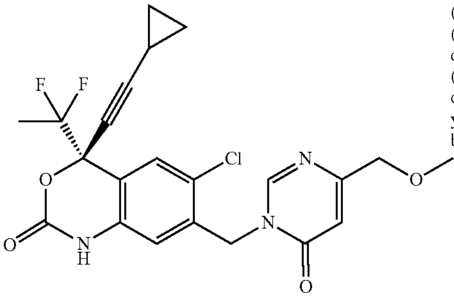 [SMILES: COCc1cc(=O)n(Cc2cc3c(cc2Cl)[C@@](C#CC2CC2)(C(C)(F)F)OC(=O)N3)cn1] | (S)-6-chloro-4-(cyclopropylethynyl)-4-(1,1-difluoroethyl)-7-((4-(methoxymethyl)-6-oxopyrimidin-1(6H)-yl)methyl)-1,4-dihydro-2H-benzo[d][1,3]oxazin-2-one | 464.2 | B04 |

TABLE 1-continued

| Ex. | Structure | IUPAC Name | MS [M + 1] | INT |
|---|---|---|---|---|
| 28 | 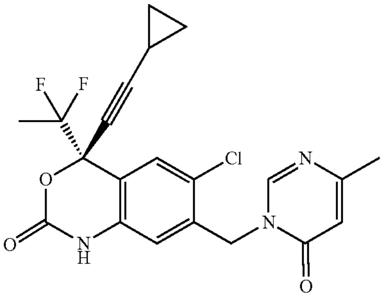 [SMILES: Cc1cc(=O)n(Cc2cc3c(cc2Cl)[C@@](C#CC2CC2)(C(C)(F)F)OC(=O)N3)cn1] | (S)-6-chloro-4-(cyclopropylethynyl)-4-(1,1-difluoroethyl)-7-((4-methyl-6-oxopyrimidin-1(6H)-yl)methyl)-1,4-dihydro-2H-benzo[d][1,3]oxazin-2-one | 434.1 | B04 |

Example 29: (S)-7-((1H-pyrazol-1-yl)methyl)-4-(cyclopropylethynyl)-6-fluoro-4-(trifluoromethyl)-1,4-dihydro-2H-benzo[d][1,3]oxazin-2-one AND (R)-7-((1H-pyrazol-1-yl)methyl-4-(cyclopropylethynyl-6-fluoro-4-(trifluoromethyl)-1,4-dihydro-2H-benzo[d][1,3]oxazin-2-one

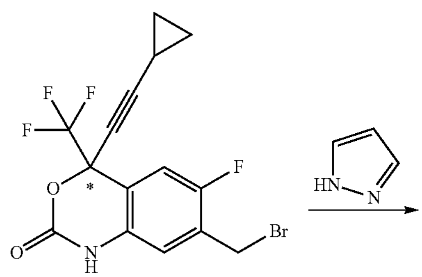

B01

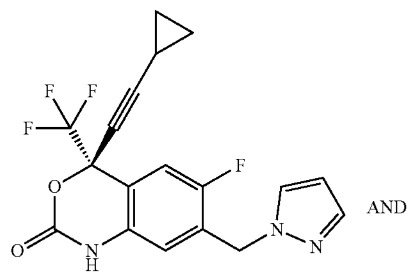

AND

29-Isomer A
faster eluting

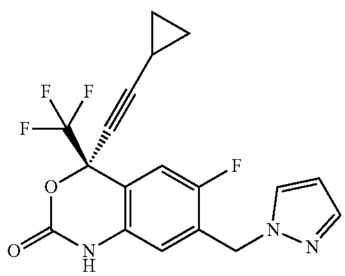

29-Isomer B
slower eluting

To a solution of pyrazole (19.58 mg, 0.288 mmol) in DMF (1 mL) was added NaH (6.90 mg, 0.288 mmol) at 0° C. for 15 min. followed by intermediate B01 (50 mg, 0.144 mmol). The mixture was stirred at 25° C. for 1 h. The mixture was quenched with $H_2O$ (10 mL), extracted with EtOAc (10 mL×2), washed with brine (10 mL), dried over $Na_2SO_4$, filtered and concentrated. The resulting residue was purified by prep-TLC (1% MeOH:DCM) followed by SFC (DAICEL CHIRALPAK AD, 15% (0.1% $NH_3H_2O$):EtOH, 55 ml/min): Isomer A (faster eluting): $^1H$ NMR (400 MHz, MeCN-$d_3$) δ 8.62 (br s, 1H), 7.65-7.64 (d, J=2.1 Hz, 1H), 7.51-7.50 (d, J=1.3 Hz, 1H), 7.32-7.30 (d, J=9.6 Hz, 1H), 6.53-6.52 (d, J=6.1 Hz, 1H), 6.33-6.32 (t, J=2.1 Hz, 1H), 5.38 (s, 2H), 1.46-1.43 (m, 1H), 0.95-0.90 (m, 2H), 0.81-0.79 (m, 2H). MS (ESI) m/z 380.0 $[M+H]^+$. AND Isomer B (slower eluting): $^1H$ NMR (400 MHz, MeCN-$d_3$) δ 8.61 (br s, 1H), 7.65-7.64 (d, J=2.3 Hz, 1H), 7.51-7.50 (d, J=1.6 Hz, 1H), 7.32-7.30 (d, J=9.6 Hz, 1H), 6.53-6.51 (d, J=6.1 Hz, 1H), 6.33-6.32 (t, J=2.1 Hz, 1H), 5.38 (s, 2H), 1.46-1.44 (m, 1H), 0.95-0.90 (m, 2H), 0.81-0.78 (m, 2H). MS (ESI) m/z 380.0 $[M+H]^+$.

Example 30: (S)-4-((4-(cyclopropylethynyl)-2-oxo-4-(trifluoromethyl)-1,4-dihydro-2H-benzo[d][1,3]oxazin-7-yl)methyl)benzenesulfonamide AND (R)-4-((4-(cyclopropylethynyl)-2-oxo-4-(trifluoromethyl)-1,4-dihydro-2H-benzo[d][1,3]oxazin-7-yl)methyl)benzenesulfonamide

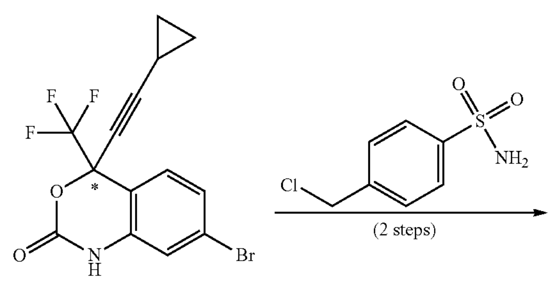

A02

-continued

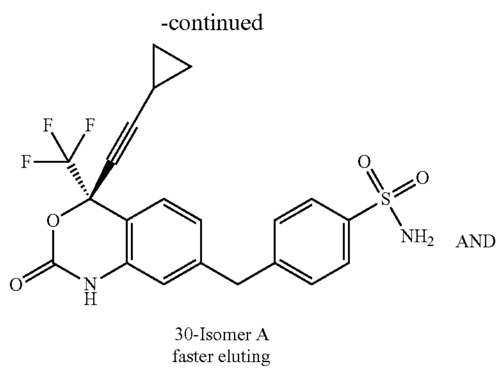

AND

30-Isomer A
faster eluting

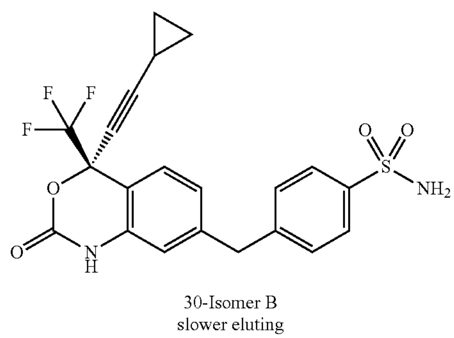

30-Isomer B
slower eluting

Step 1. 4-(cyclopropylethynyl)-7-(4,4,5,5-tetramethyl-1,3,2-dioxaborolan-2-yl)-4-(trifluoromethyl)-1H-benzo[d][1,3]oxazin-2(4H)-one: A mixture of intermediate A02 (170 mg, 0.472 mmol), $PdC_2(dppf)$ (34.5 mg, 0.047 mmol), BisPin (144 mg, 0.566 mmol) and KOAc (139 mg, 1.416 mmol) in 1,4-dioxane (5 ml) was stirred at 80° C. for 2 h. The mixture was filtered and purified by pre-HPLC (water: MeCN with 0.1% TFA) to give the title compound. MS (ESI) m/z 408 $[M+H]^+$.

Step 2. (S)-4-((4-(cyclopropylethynyl)-2-oxo-4-(trifluoromethyl)-2,4-dihydro-1H-benzo[d][1,3]oxazin-7-ylmethyl)benzenesulfonamide AND (R)-4-((4-(cyclopropylethynyl)-2-oxo-4-(trifluoromethyl)-2,4-dihydro-1H-benzo[d][1,3]oxazin-7-yl)methyl)benzenesulfonamide: To a solution of 4-(cyclopropylethynyl)-7-(4,4,5,5-tetramethyl-1,3,2-dioxaborolan-2-yl)-4-(trifluoromethyl)-H-benzo[d][1,3]oxazin-2(4H)-one (40 mg, 0.123 mmol) in 1,4-dioxane (2 ml) and water (0.5 ml) was added $Cs_2CO_3$ (160 mg, 0.492 mmol), 4-(chloromethyl)benzenesulfonamide (50.6 mg, 0.246 mmol) and $PdC_2(dppf)$ (13.51 mg, 0.018 mmol). The reaction was stirred at 90° C. for 3 h under $N_2$. The mixture was filtered and directly purified by pre-HPLC (water: MeCN with 0.1% TFA) followed by SFC (DAICEL CHIRALPAK AD, 45% (0.1% $NH_3H_2O$):EtOH, 75 ml/min): Isomer A (faster eluting): $^1H$ NMR (400 MHz, MeCN-$d_3$) δ 0.75-0.84 (m, 2H) 0.89-0.96 (m, 2H) 1.36-1.62 (m, 1H) 4.09 (s, 2H) 5.66 (br s, 1H) 6.79 (s, 1H) 7.06 (br d, J=8.16 Hz, 1H) 7.31-7.60 (m, 3H) 7.83 (d, J=8.38 Hz, 2H). MS (ESI) m/z 451.1 $[M+H]^+$ AND Isomer B (slow eluting): $^1H$ NMR (400 MHz, MeCN-$d_3$) δ 0.71-0.84 (m, 2H) 0.89-0.96 (m, 2H) 1.40-1.53 (m, 1H) 3.91-4.32 (m, 2H) 5.66 (br s, 1H) 6.79 (s, 1H) 7.06 (d, J=8.16 Hz, 1H) 7.27-7.56 (m, 3H) 7.83 (d, J=8.38 Hz, 2H). MS (ESI) m/z 451.1 $[M+H]^+$.

Example 31: (S)-7-((2-aminopyrimidin-4-yl)methyl)-4-(cyclopropylethynyl)-6-fluoro-4-(trifluoromethyl)-1,4-dihydro-2H-benzo[d][1,3]oxazin-2-one AND (R)-7-((2-aminopyrimidin-4-ylmethyl)-4-(cyclopropylethynyl-6-fluoro-4-(trifluoromethyl)-1,4-dihydro-2H-benzo[d][1,3]oxazin-2-one

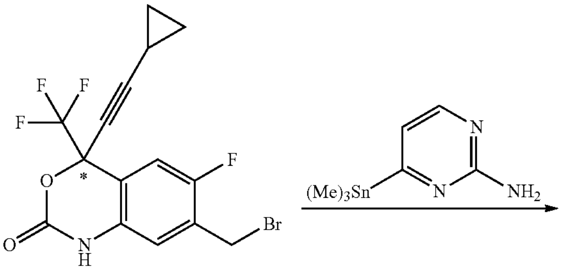

B01

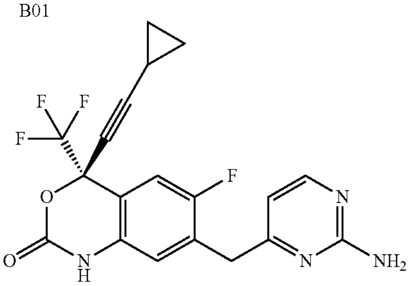

AND

31-Isomer A
faster eluting

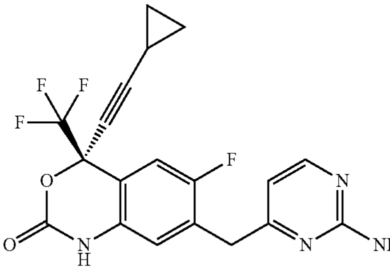

31-Isomer B
slower eluting

To a solution of 4-chloropyrimidin-2-amine (80 mg, 0.618 mmol) and 1,1,1,2,2,2-hexamethyldistannane (170 mg, 0.518 mmol) in 1,4-dioxane (3 mL) were added $Pd(PPh_3)_4$ (71.4 mg, 0.062 mmol) under $N_2$. The reaction was stirred at 105° C. for 16 h under $N_2$. Then, intermediate B01 (100 mg, 0.255 mmol), CuI (48.6 mg, 0.255 mmol) and $Pd(PPh_3)_4$ (147 mg, 0.128 mmol) were added under $N_2$. The resulting mixture was stirred at 100° C. for 2 h. The mixture was filtered and purified by pre-HPLC (water:MeCN with 0.1% TFA) followed by SFC (DAICEL CHIRALPAK AD, 35% (0.1% $NH_3H_2O$):EtOH, 60 ml/min): Isomer A (faster eluting): $^1H$ NMR (400 MHz, $CDCl_3$) δ=8.23-8.21 (d, J=5.1 Hz, 1H), 7.83 (s, 1H), 7.25 (s, 1H), 6.70-6.68 (d, J=5.9 Hz, 1H), 6.53-6.51 (d, J=5.0 Hz, 1H), 5.11 (br s, 2H), 3.97-3.86 (q, J=15.1 Hz, 2H), 1.39-1.38 (m, 1H), 0.93-0.90 (m, 2H), 0.87-0.84 (m, 2H). MS (ESI) m/z 407.1 $[M+H]^+$ AND Isomer B (slow eluting): $^1H$ NMR (400 MHz, $CDCl_3$) δ=8.25-8.24 (d, J=5.3 Hz, 1H), 8.04 (br s, 1H), 7.25 (s, 1H), 6.82-6.81 (d, J=5.9 Hz, 1H), 6.59-6.58 (d, J=5.3 Hz, 1H), 5.59 (br s, 2H), 4.02-3.91 (q, J=15.1 Hz, 2H), 1.39-1.36 (m, 1H), 0.93-0.90 (m, 2H), 0.86-0.84 (m, 2H). MS (ESI) m/z 407.1 $[M+H]^+$.

Example 32: (S)-2-amino-4-((4-(cyclopropylethynyl)-6-fluoro-2-oxo-4-(trifluoromethyl)-1,4-dihydro-2H-benzo[d][1,3]oxazin-7-yl)methyl)nicotinonitrile AND (R)-2-amino-4-((4-(cyclopropylethynyl)-6-fluoro-2-oxo-4-(trifluoromethyl)-1,4-dihydro-2H-benzo[d][1,3]oxazin-7-ylmethyl)nicotinonitrile

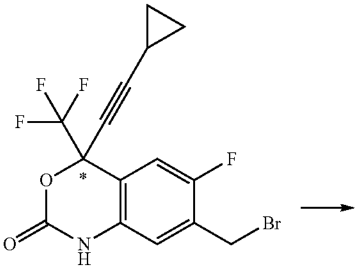

B01

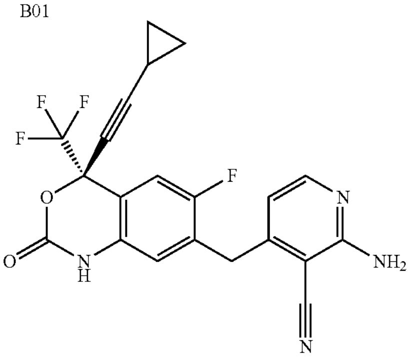

AND

32-Isomer A
faster eluting

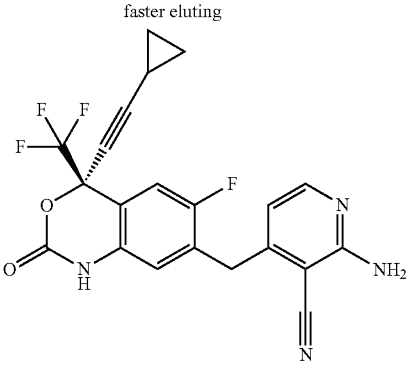

32-Isomer B
slower eluting

DMA (1.5 mL) was added to a mixture of intermediate B01 (20 mg, 0.051 mmol), intermediate $CO_2$ (20.20 mg, 0.102 mmol), $NiCl_2$(DME) (2.80 mg, 0.013 mmol), picolinimidamide (6.18 mg, 0.051 mmol), manganese (11.21 mg, 0.204 mmol) and TBAI (4.33 mg, 0.012 mmol) in the glove box. The reaction was stirred at 70° C. for 2 h. The solution was poured into water (10 mL) and extracted with EA (10 mL×2). The organic layer was washed with water (10 mL), brine (20 mL), dried over $Na_2SO_4$, filtered and concentrated. The crude was purified by pre-HPLC prep-HPLC (water with 10 mM $NH_4HCO_3$:MeCN) followed by SFC (DAICEL CHIRALPAK AD, 45% (0.1% $NH_3H_2O$):EtOH, 75 ml/min): Isomer A (faster eluting): $^1H$ NMR (400 MHz, MeOH-$d_4$) δ ppm 8.07 (d, J=5.75 Hz, 1H) 7.29 (d, J=9.41 Hz, 1H) 6.86 (d, J=6.24 Hz, 1H) 6.64 (d, J=5.75 Hz, 1H) 4.18 (s, 2H) 1.48 (tt, J=8.33, 5.00 Hz, 1H) 1.02-0.90 (m, 2H) 0.85-0.72 (m, 2H). MS (ESI) m/z 431.1 $[M+H]^+$ AND Isomer B (slower eluting): $^1H$ NMR (400 MHz, MeOH-$d_4$) δ ppm 8.07 (d, J=5.75 Hz, 1H) 7.29 (d, J=9.41 Hz, 1H) 6.86 (d, J=6.24 Hz, 1H) 6.64 (d, J=5.75 Hz, 1H) 4.18 (s, 2H) 1.48 (tt, J=8.33, 5.00 Hz, 1H) 1.02-0.90 (m, 2H) 0.85-0.72 (m, 2H). MS (ESI) m/z 431.1 $[M+H]^+$.

Example 33: (S)-2-amino-4-((6-chloro-4-(cyclopropylethynyl)-2-oxo-4-(trifluoromethyl)-1,4-dihydro-2H-benzo[d][1,3]oxazin-7-yl)methyl)nicotinonitrile

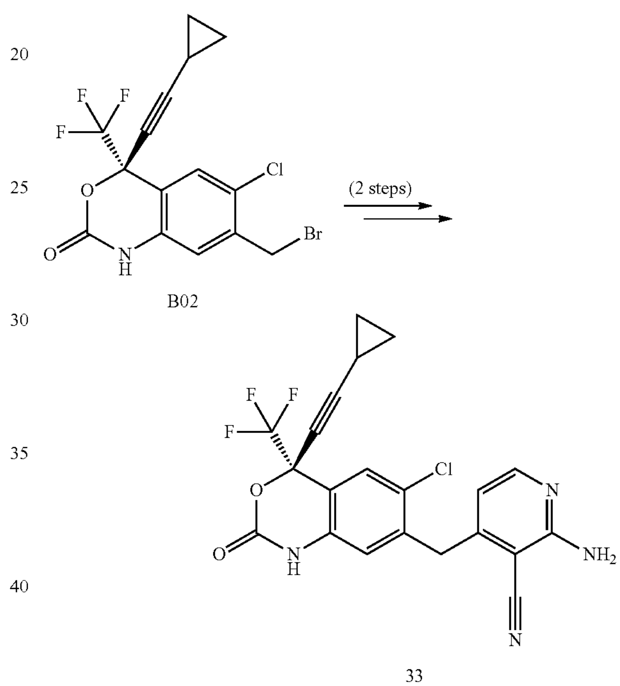

B02

33

Step 1: (S)-6-chloro-7-(chloromethyl)-4-(cyclopropylethynyl)-4-(trifluoromethyl)-1,4-dihydro-2H-benzo[d][1,3]oxazin-2-one. To a mixture of intermediate B02 (100 mg, 0.245 mmol) in DMF (1.5 mL) was added LiCl (51.9 mg, 1.224 mmol) and the mixture was stirred at 15° C. for 2 h under $N_2$. The reaction was quenched with water (5 mL) and extracted with EA (5 mL). The organic layer was concentrated and purified by prep-TLC ($SiO_2$, PE:EA=3:1) to give the title compound. MS (ESI) m/z 364.0 $[M+H]^+$ Step 2: (S)-2-amino-4-((6-chloro-4-(cyclopropylethynyl)-2-oxo-4-(trifluoromethyl)-1,4-dihydro-2H-benzo[d][1,3]oxazin-7-yl)methyl)nicotinonitrile. To a solution of (S)-6-chloro-7-(chloromethyl)-4-(cyclopropylethynyl)-4-(trifluoromethyl)-1,4-dihydro-2H-benzo[d][1,3]oxazin-2-one (10 mg, 0.027 mmol) and intermediate $CO_2$ (7.07 mg, 0.036 mmol) in DMA (1 mL) were added $NiCl_2$(DME) (1.207 mg, 5.49 μmol), picolinimidamide (0.665 mg, 5.49 μmol), NaI (4.12 mg, 0.027 mmol and Zn (4.49 mg, 0.069 mmol) in a dry glove box. The reaction was stirred at 25° C. for 2 h. The reaction mixture was poured into water (10 mL) and extracted with EA (10 mL×2). The combined organic layers were washed with brine (5 mL×2), dried over $Na_2SO_4$, filtered and concentrated. The crude was purified by prep-HPLC (water with 10 mM $NH_4HCO_3$:MeCN) to give the title compound. $^1H$ NMR (400 MHz, MeCN-$d_3$) δ=8.43 (s, 1H), 8.12 (d, J=5.0 Hz, 1H), 7.58 (s, 1H), 6.73 (s, 1H), 6.43 (d, J=5.3 Hz, 1H), 5.70 (br s, 2H), 4.15 (s, 2H), 1.53-1.39 (m, 1H), 0.93 (dd, J=3.5, 8.3 Hz, 2H), 0.85-0.69 (m, 2H). MS (ESI) m/z 447.0 $[M+H]^+$.

The compounds in Table 2 were prepared in an analogous fashion to that described for Example 33.

TABLE 2

| Ex. | Structure | IUPAC Name | MS [M + 1] | INT. |
|---|---|---|---|---|
| 34 | 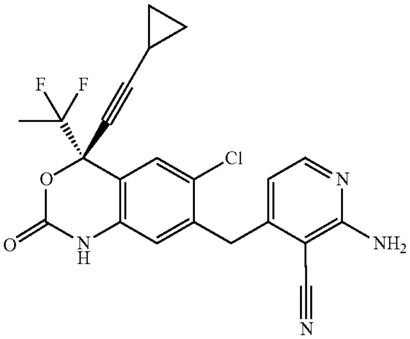 [SMILES: CC(F)(F)[C@@]1(C#CC2CC2)OC(=O)Nc2cc(Cc3ccnc(N)c3C#N)c(Cl)cc21] | (S)-2-amino-4-((6-chloro-4-(cyclopropylethynyl)-4-(1,1-difluoroethyl)-2-oxo-1,4-dihydro-2H-benzo[d][1,3]oxazin-7-yl)methyl)nicotinonitrile | 443.1 | B04 |
| 35 | 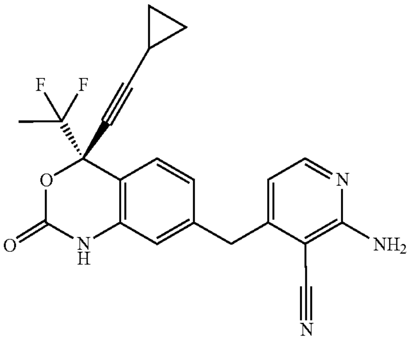 [SMILES: CC(F)(F)[C@@]1(C#CC2CC2)OC(=O)Nc2cc(Cc3ccnc(N)c3C#N)ccc21] | (S)-2-amino-4-((4-(cyclopropylethynyl)-4-(1,1-difluoroethyl)-2-oxo-1,4-dihydro-2H-benzo[d][1,3]oxazin-7-yl)methyl)nicotinonitrile | 409.1 | B04 |
| 36 | 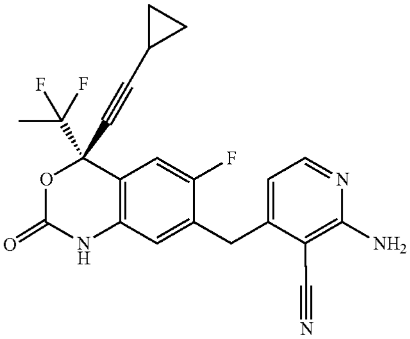 [SMILES: CC(F)(F)[C@@]1(C#CC2CC2)OC(=O)Nc2cc(Cc3ccnc(N)c3C#N)c(F)cc21] | (S)-2-amino-4-((4-(cyclopropylethynyl)-4-(1,1-difluoroethyl)-6-fluoro-2-oxo-1,4-dihydro-2H-benzo[d][1,3]oxazin-7-yl)methyl)nicotinonitrile | 427.2 | B05 |

Example 37: (S)-7-((2-aminopyrimidin-4-yl)methyl)-4-(cyclopropylethynyl)-4-(1,1-difluoroethyl)-1,4-dihydro-2H-benzo[d][1,3]oxazin-2-one

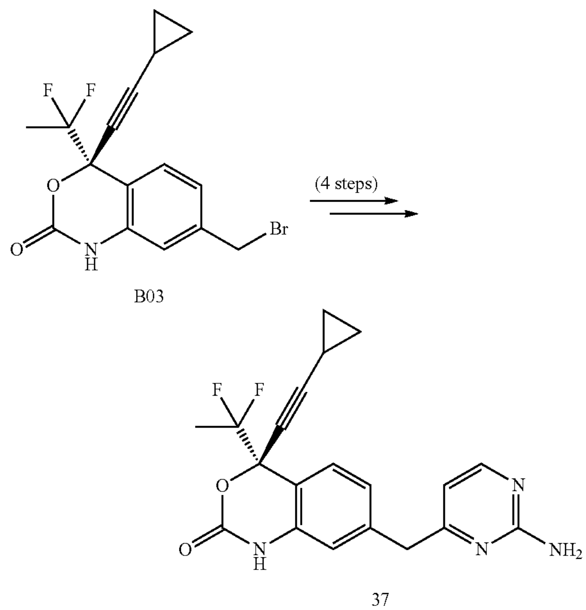

B03

37

Step 1: (S)-7-(chloromethyl)-4-(cyclopropylethynyl)-4-(1,1-difluoroethyl)-1,4-dihydro-2H-benzo[d][1,3]oxazin-2-one. To a mixture of intermediate B03 (260 mg, 0.70 mmol) in DMF (5 mL) was added LiCl (149 mg, 3.51 mmol) and the mixture was stirred at 25° C. for 16 h. The reaction was quenched with water (50 mL) and extracted with EA (30 mL×3). The combined organic layer was washed with brine (30 mL), dried over $Na_2SO_4$, filtered and concentrated. The residue was purified by pre-TLC ($SiO_2$, PE:EA=3:1) to give the title compound.

Step 2: (S)-7-(2-chloropyrimidin-4-ylmethyl)-4-(cyclopropylethynyl)-4-(1,1-difluoroethyl)-6-fluoro-1,4-dihydro-2H-benzo[d][1,3]oxazin-2-one. To a solution of (S)-7-(chloromethyl)-4-(cyclopropylethynyl)-4-(1,1-difluoroethyl)-1,4-dihydro-2H-benzo[d][1,3]oxazin-2-one (100 mg, 0.31 mmol) and 2,4-dichloropyrimidine (91.5 mg, 0.61 mmol) in DMA (10 mL) was added $NiCl_2$(DME) (16.9 mg, 76.7 μmol), picolinimidamide (93.0 mg, 0.77 mmol)), Zn (44.2 mg, 0.68 mmol) and NaI (46.0 mg, 0.31 mmol) in a dry glove box. The reaction was stirred at 20° C. for 2 h. The reaction was quenched with water (100 mL), extracted with EA (50 mL×2). The combined organic layers were washed with brine (100 mL), dried with $Na_2SO_4$, filtered and concentrated. The residue was purified by pre-TLC ($SiO_2$, PE:EA=3:1) to give the title compound.

Step 3: tert-butyl (S)-(4-((4-(cyclopropylethynyl)-4-(1,1-difluoroethyl)-2-oxo-1,4-dihydro-2H-benzo[d][1,3]oxazin-7-ylmethyl)pyrimidin-2-yl)carbamate. To a solution of (S)-7-((2-chloropyrimidin-4-yl)methyl)-4-(cyclopropylethynyl)-4-(1,1-difluoroethyl)-1,4-dihydro-2H-benzo[d][1,3]oxazin-2-one (70 mg, 0.173 mmol) and tert-butyl carbamate (40.6 mg, 0.347 mmol) in toluene (6 mL) was added NaOtBu (33.3 mg, 0.347 mmol), XPhos Pd G3 (14.67 mg, 0.017 mmol) in a dry glove box. The reaction was stirred at 100° C. for 1 h. The reaction mixture was quenched with water (10 mL) and extracted with EA (10 mL×2). The combined organic layers were washed with brine (20 mL), dried over $Na_2SO_4$, filtered and concentrated. The residue was purified by pre-TLC ($SiO_2$, PE:EA=1:2) to give the title compound.

Step 4: (S)-7-((2-aminopyrimidin-4-yl)methyl)-4-(cyclopropylethynyl)-4-(1,1-difluoroethyl)-1,4-dihydro-2H-benzo[d][1,3]oxazin-2-one. To a solution of tert-butyl (S)-(4-((4-(cyclopropylethynyl)-4-(1,1-difluoroethyl)-2-oxo-1,4-dihydro-2H-benzo[d][1,3]oxazin-7-yl)methyl)pyrimidin-2-yl)carbamate (20 mg, 0.041 mmol) in DCM (2 mL) was added TFA (0.5 mL). The reaction was stirred at 20° C. for 2 h. The mixture was concentrated and purified by prep-HPLC (water:MeCN with 0.1% TFA) to give the title compound. $^1$H NMR (400 MHz, MeCN-$d_3$) δ=8.29 (br s, 1H), 8.16 (d, J=5.9 Hz, 1H), 7.44 (d, J=8.1 Hz, 1H), 7.04 (d, J=8.0 Hz, 1H), 6.79 (s, 1H), 6.70 (d, J=5.9 Hz, 1H), 4.02 (s, 2H), 1.80 (t, J=18.9 Hz, 3H), 1.46-1.36 (m, 1H), 0.93-0.83 (m, 2H), 0.81-0.69 (m, 2H). MS (ESI) m/z 385.1 $[M+H]^+$.

The compounds in Table 3 were prepared in an analogous fashion to that described for Example 37.

TABLE 3

| Ex. | Structure | IUPAC Name | MS [M + 1] | INT. |
|---|---|---|---|---|
| 38 | 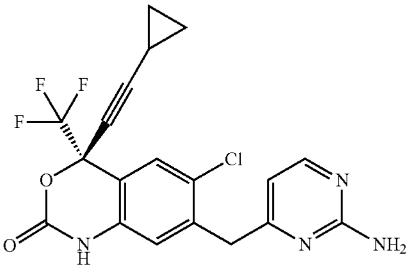 [SMILES: Nc1nccc(Cc2cc3c(cc2Cl)[C@@](C#CC2CC2)(C(F)(F)F)OC(=O)N3)n1] | (S)-7-((2-aminopyrimidin-4-yl)methyl)-6-chloro-4-(cyclopropylethynyl)-4-(trifluoromethyl)-1,4-dihydro-2H-benzo[d][1,3]oxazin-2-one | 423.0 | B02 |

TABLE 3-continued

| Ex. | Structure | IUPAC Name | MS [M + 1] | INT. |
|---|---|---|---|---|
| 39 | 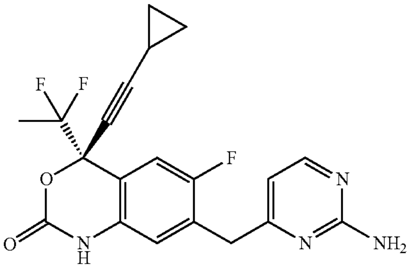 [SMILES: CC(F)(F)[C@@]1(C#CC2CC2)OC(=O)Nc2cc(Cc3ccnc(N)n3)c(F)cc21] | (S)-7-((2-aminopyrimidin-4-yl)methyl)-4-(cyclopropylethynyl)-4-(1,1-difluoroethyl)-6-fluoro-1,4-dihydro-2H-benzo[d][1,3]oxazin-2-one | 403.1 | B05 |
| 40 | 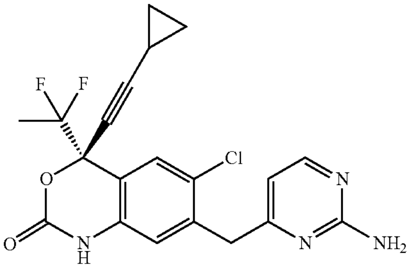 [SMILES: CC(F)(F)[C@@]1(C#CC2CC2)OC(=O)Nc2cc(Cc3ccnc(N)n3)c(Cl)cc21] | (S)-7-((2-aminopyrimidin-4-yl)methyl)-6-chloro-4-(cyclopropylethynyl)-4-(1,1-difluoroethyl)-1,4-dihydro-2H-benzo[d][1,3]oxazin-2-one | 419.1 | B04 |

Determination of Cell Kill (HIV-TACK) Activity:

PBMCs derived from healthy donors were grown in complete media (RPMI 1640 with L-glutamine; 10% heat inactivated Fetal Bovine Serum; 100 U/mL Penicillin-Streptomycin) containing 5 μg/mL Phytohemagglutinin at about $2.5\times10^6$ cells/mL for 3 days at 5% $CO_2$, 37° C., and 90% humidity. On day 4, PHA stimulated cells were washed and resuspended at about $20\times10^6$ cells/mL in complete media with IL-2 (10 U/mL) with VSV-G pseudotyped HIV virus stock (VSV-G/pNLG1-P2A-ΔEnv-20 μg/mL p24) and incubated for 4 hours at 37° C., 5% $CO_2$ and 90% humidity. VSV-G/pNLG1-P2A-ΔEnv is a VSV-G pseudotyped virus derived from pNL43 with egfp inserted 5' of nef and eGFP expression driven off normal spliced RNA transcripts. Virus contained Vif truncated by 50 amino acids due to deletion of a single nucleotide causing a frameshift and does not express Nef due to a stop codon after gfp. HIV Env is not expressed due to a frameshift resulting in multiple stop codons. Infected cells were then washed with complete media plus 10 U/mL IL-2 3-times with centrifuging at 200×g for 3 minutes at 22° C. Cells were resuspended at $5\times10^6$ cells/mL in complete media plus 10 U/mL IL-2 and incubated overnight at 37° C., 5% $CO_2$ and 90% humidity. For compound treatment infected PBMCs were diluted to $4\times10^5$ cells/mL with RPMI 1640 with L-glutamine, 50% Normal Human Serum (NHS), 100 U/mL Penicillin-Streptomycin plus IL-2 (10 U/mL) and 20,000 cells were transferred to each well in a 384-well poly-D-lysine coated compound plate containing compounds with final DMSO<0.5%. Compounds were tested with 10-point 3-fold titration. Plates were analyzed on an Acumen ex3 imager using the Blue Laser 488 nm and the number of GFP positive objects were collected with loss of GFP representing death of infected cells. Titration curves and $EC_{50}$ values were calculated using a four-parameter logistic fit. Results are shown in Table 4.

TABLE 4

| Ex. No. | TACK EC50 (nM) |
|---|---|
| 1A | 39 |
| 2A | 88 |
| 3A | 46 |
| 4A | 25 |
| 5A | 35 |
| 6A | 43 |
| 7A | 45 |
| 8 | 30 |
| 9 | 90 |
| 10 | 66 |
| 11 | 47 |
| 12 | 68 |
| 13 | 11 |
| 14 | 63 |
| 15 | 63 |
| 16 | 113 |
| 17 | 92 |
| 18 | 83 |
| 19 | 128 |
| 20 | 11 |
| 21 | 12 |
| 22 | 12 |
| 23 | 16 |
| 24 | 9 |
| 25 | 37 |
| 26 | 16 |
| 27 | 16 |
| 28 | 15 |
| 29A | 428 |
| 30A | 755 |
| 31A | 91 |
| 32A | 111 |
| 33 | 213 |
| 34 | 76 |
| 35 | 20 |
| 36 | 18 |
| 37 | 43 |
| 38 | 149 |
| 39 | 16 |
| 40 | 65 |

What is claimed is:

1. A compound of Formula I:

I

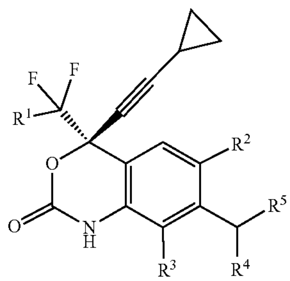

or a pharmaceutically acceptable salt thereof, wherein:

$R^1$ is halo or —$C_{1-8}$alkyl unsubstituted or substituted with 1 to 7 of —F;

$R^2$ is —H, halo, —CN, —$C_{1-8}$alkyl, —$C_{2-8}$alkenyl, —C(O)O$C_{1-8}$alkyl, —C(O)$C_{1-8}$alkyl or —$NR^6R^7$;

$R^3$ is —H or halo;

$R^4$ is —H or halo;

$R^5$ is a 5 or 6-membered ring selected from phenyl, pyrimidinyl, pyrimidinone, pyrazinone, pyrazolyl and pyridinyl, wherein each ring is unsubstituted or substituted with one or more substituents up to the maximum number allowed by valence, independently selected at each occurrence from:

(i) halo, (ii) —CN, (iii) —$NR^6R^7$, (iv) —$SO_2$—$NR^6R^7$, (v) —$C_{1-8}$alkyl unsubstituted or substituted with 1 to 8 substituents independently selected at each occurrence from —OH and halo, (vi) —$C_{1-4}$alkyl-O—$C_{1-4}$alkyl unsubstituted or substituted with 1 to 8 substituents independently selected at each occurrence from —OH or halo, and (vii) —O$C_{1-8}$alkyl unsubstituted or substituted with 1 to 8 substituents independently selected at each occurrence from —OH and halo;

$R^6$ is —H or —$C_{1-8}$alkyl unsubstituted or substituted with 1 to 8 substituents independently selected at each occurrence from —OH and halo; and $R^7$ is —H or —$C_{1-8}$alkyl unsubstituted or substituted with 1 to 8 substituents independently selected at each occurrence from —OH and halo.

2. The compound of claim 1 wherein $R^1$ is halo or —$C_{1-6}$alkyl, or a pharmaceutically acceptable salt thereof.

3. The compound of claim 2 wherein $R^2$ is —H, halo, —CN, —$C_{1-6}$alkyl, —$C_{2-6}$alkenyl, —C(O)O—$C_{1-6}$alkyl, —C(O)—$C_{1-6}$alkyl, or —$NR^6R^7$, or a pharmaceutically acceptable salt thereof.

4. The compound of claim 3 wherein $R^3$ is —H, F, Cl or Br, or a pharmaceutically acceptable salt thereof.

5. The compound of claim 4 wherein $R^4$ is —H, F, Cl or Br, or a pharmaceutically acceptable salt thereof.

6. The compound claim 5 wherein $R^6$ and $R^7$ are each independently selected from —H and —$C_{1-6}$alkyl, or a pharmaceutically acceptable salt thereof.

7. The compound claim 6, or a pharmaceutically acceptable salt thereof, wherein $R^5$ is selected from:

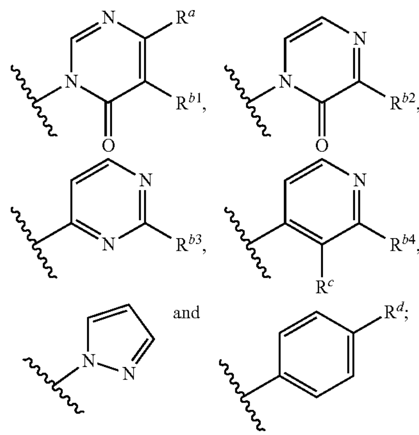

and wherein:

$R^a$ is (i) —H, (ii) —$C_{1-6}$alkyl, (iii) —$C_{1-3}$alkyl substituted with 1-7 of halo, (iv) —$C_{1-3}$alkyl-O—$C_{1-3}$alkyl, or (v) —O$C_{1-6}$alkyl;

$R^{b1}$, $R^{b2}$, $R^{b3}$ and $R^{b4}$ are each independently selected from (i) —H or (ii) —$NR^6R^7$;

$R^c$ is (i) —H, (ii) halo or (iii) —CN; and $R^d$ is (i) —$C_{1-6}$alkyl, (ii) —$C_{1-3}$alkyl substituted with 1-7 of halo, or (iii) —$S(O)_2NR^6R^7$.

8. The compound of claim 1 that is:

(S)-7-((3-amino-2-oxopyrazin-1(2H)-yl)methyl)-4-(cyclopropylethynyl)-6-fluoro-4-(trifluoromethyl)-1,4-dihydro-2H-benzo[d][1,3]oxazin-2-one;

(S)-4-(cyclopropylethynyl)-6-fluoro-7-((6-oxopyrimidin-1(6H)-yl)methyl)-4-(trifluoromethyl)-1,4-dihydro-2H-benzo[d][1,3]oxazin-2-one;

(S)-7-((5-amino-6-oxopyrimidin-1(6H)-yl)methyl)-4-(cyclopropylethynyl)-6-fluoro-4-(trifluoromethyl)-1,4-dihydro-2H-benzo[d][1,3]oxazin-2-one;

(S)-4-(cyclopropylethynyl)-6-fluoro-7-((4-methoxy-6-oxopyrimidin-1(6H)-yl)methyl)-4-(trifluoromethyl)-1,4-dihydro-2H-benzo[d][1,3]oxazin-2-one;

(S)-4-(cyclopropylethynyl)-6-fluoro-7-((4-(methoxymethyl)-6-oxopyrimidin-1(6H)-yl)methyl)-4-(trifluoromethyl)-1,4-dihydro-2H-benzo[d][1,3]oxazin-2-one;

(S)-4-(cyclopropylethynyl)-6-fluoro-7-((4-methyl-6-oxopyrimidin-1(6H)-yl)methyl)-4-(trifluoromethyl)-1,4-dihydro-2H-benzo[d][1,3]oxazin-2-one;

(S)-4-(cyclopropylethynyl)-7-((4-(difluoromethyl)-6-oxopyrimidin-1(6H)-yl)methyl)-6-fluoro-4-(trifluoromethyl)-1,4-dihydro-2H-benzo[d][1,3]oxazin-2-one;

(S)-7-((3-amino-2-oxopyrazin-1(2H)-yl)methyl)-4-(cyclopropylethynyl)-4-(1,1-difluoroethyl)-1,4-dihydro-2H-benzo[d][1,3]oxazin-2-one;

(S)-4-(cyclopropylethynyl)-4-(1,1-difluoroethyl)-7-((6-oxopyrimidin-1(6H)-yl)methyl)-1,4-dihydro-2H-benzo[d][1,3]oxazin-2-one;

(S)-4-(cyclopropylethynyl)-4-(1,1-difluoroethyl)-7-((4-methyl-6-oxopyrimidin-1(6H)-yl)methyl)-1,4-dihydro-2H-benzo[d][1,3]oxazin-2-one;

(S)-4-(cyclopropylethynyl)-4-(1,1-difluoroethyl)-7-((4-methoxy-6-oxopyrimidin-

-continued

1(6H)-yl)methyl)-1,4-dihydro-2H-benzo[d][1,3]oxazin-2-one;
(S)-4-(cyclopropylethynyl)-4-(1,1-difluoroethyl)-7-((4-(methoxymethyl)-6-oxopyrimidin-1(6H)-yl)methyl)-1,4-dihydro-2H-benzo[d][1,3]oxazin-2-one;
(S)-6-chloro-4-(cyclopropylethynyl)-4-(1,1-difluoroethyl)-7-((4-methoxy-6-oxopyrimidin-1(6H)-yl)methyl)-1,4-dihydro-2H-benzo[d][1,3]oxazin-2-one;
(S)-6-chloro-4-(cyclopropylethynyl)-7-((4-methoxy-6-oxopyrimidin-1(6H)-yl)methyl)-4-(trifluoromethyl)-1,4-dihydro-2H-benzo[d][1,3]oxazin-2-one;
(S)-6-chloro-4-(cyclopropylethynyl)-7-((6-oxopyrimidin-1(6H)-yl)methyl)-4-(trifluoromethyl)-1,4-dihydro-2H-benzo[d][1,3]oxazin-2-one;
(S)-7-((3-amino-2-oxopyrazin-1(2H)-yl)methyl)-6-chloro-4-(cyclopropylethynyl)-4-(trifluoromethyl)-1,4-dihydro-2H-benzo[d][1,3]oxazin-2-one;
(S)-6-chloro-4-(cyclopropylethynyl)-7-((4-methyl-6-oxopyrimidin-1(6H)-yl)methyl)-4-(trifluoromethyl)-1,4-dihydro-2H-benzo[d][1,3]oxazin-2-one;
(S)-6-chloro-4-(cyclopropylethynyl)-7-((4-(difluoromethyl)-6-oxopyrimidin-1(6H)-yl)methyl)-4-(trifluoromethyl)-1,4-dihydro-2H-benzo[d][1,3]oxazin-2-one;
(S)-6-chloro-4-(cyclopropylethynyl)-7-((4-(methoxymethyl)-6-oxopyrimidin-1(6H)-yl)methyl)-4-(trifluoromethyl)-1,4-dihydro-2H-benzo[d][1,3]oxazin-2-one;
(S)-7-((5-amino-6-oxopyrimidin-1(6H)-yl)methyl)-4-(cyclopropylethynyl)-4-(1,1-difluoroethyl)-6-fluoro-1,4-dihydro-2H-benzo[d][1,3]oxazin-2-one;
(S)-7-((3-amino-2-oxopyrazin-1(2H)-yl)methyl)-4-(cyclopropylethynyl)-4-(1,1-difluoroethyl)-6-fluoro-1,4-dihydro-2H-benzo[d][1,3]oxazin-2-one;
(S)-4-(cyclopropylethynyl)-4-(1,1-difluoroethyl)-6-fluoro-7-((6-oxopyrimidin-1(6H)-yl)methyl)-1,4-dihydro-2H-benzo[d][1,3]oxazin-2-one;
(S)-4-(cyclopropylethynyl)-4-(1,1-difluoroethyl)-6-fluoro-7-((4-(methoxymethyl)-6-oxopyrimidin-1(6H)-yl)methyl)-1,4-dihydro-2H-benzo[d][1,3]oxazin-2-one;
(S)-4-(cyclopropylethynyl)-4-(1,1-difluoroethyl)-6-fluoro-7-((4-methoxy-6-oxopyrimidin-1(6H)-yl)methyl)-1,4-dihydro-2H-benzo[d][1,3]oxazin-2-one;
(S)-7-((3-amino-2-oxopyrazin-1(2H)-yl)methyl)-6-chloro-4-(cyclopropylethynyl)-4-(1,1-difluoroethyl)-1,4-dihydro-2H-benzo[d][1,3]oxazin-2-one;
(S)-6-chloro-4-(cyclopropylethynyl)-4-(1,1-difluoroethyl)-7-((6-oxopyrimidin-1(6H)-yl)methyl)-1,4-dihydro-2H-benzo[d][1,3]oxazin-2-one;
(S)-6-chloro-4-(cyclopropylethynyl)-4-(1,1-difluoroethyl)-7-((4-(methoxymethyl)-6-oxopyrimidin-1(6H)-yl)methyl)-1,4-dihydro-2H-benzo[d][1,3]oxazin-2-one;
(S)-6-chloro-4-(cyclopropylethynyl)-4-(1,1-difluoroethyl)-7-((4-methyl-6-oxopyrimidin-1(6H)-yl)methyl)-1,4-dihydro-2H-benzo[d][1,3]oxazin-2-one;
(S)-7-((1H-pyrazol-1-yl)methyl)-4-(cyclopropylethynyl)-6-fluoro-4-(trifluoromethyl)-1,4-dihydro-2H-benzo[d][1,3]oxazin-2-one;
(S)-4-((4-(cyclopropylethynyl)-2-oxo-4-(trifluoromethyl)-1,4-dihydro-2H-benzo[d][1,3]oxazin-7-yl)methyl)benzenesulfonamide;
(S)-7-((2-aminopyrimidin-4-yl)methyl)-4-(cyclopropylethynyl)-6-fluoro-4-(trifluoromethyl)-1,4-dihydro-2H-benzo[d][1,3]oxazin-2-one;
(S)-2-amino-4-((4-(cyclopropylethynyl)-6-fluoro-2-oxo-4-(trifluoromethyl)-1,4-dihydro-2H-benzo[d][1,3]oxazin-7-yl)methyl)nicotinonitrile;
(S)-2-amino-4-((6-chloro-4-(cyclopropylethynyl)-2-oxo-4-(trifluoromethyl)-1,4-dihydro-2H-benzo[d][1,3]oxazin-7-yl)methyl)nicotinonitrile;
(S)-2-amino-4-((6-chloro-4-(cyclopropylethynyl)-4-(1,1-difluoroethyl)-2-oxo-1,4-dihydro-2H-benzo[d][1,3]oxazin-7-yl)methyl)nicotinonitrile;
(S)-2-amino-4-((4-(cyclopropylethynyl)-4-(1,1-difluoroethyl)-2-oxo-1,4-dihydro-2H-benzo[d][1,3]oxazin-7-yl)methyl)nicotinonitrile;
(S)-2-amino-4-((4-(cyclopropylethynyl)-4-(1,1-difluoroethyl)-6-fluoro-2-oxo-1,4-dihydro-2H-benzo[d][1,3]oxazin-7-yl)methyl)nicotinonitrile;
(S)-7-((2-aminopyrimidin-4-yl)methyl)-4-(cyclopropylethynyl)-4-(1,1-difluoroethyl)-1,4-dihydro-2H-benzo[d][1,3]oxazin-2-one;
(S)-7-((2-aminopyrimidin-4-yl)methyl)-6-chloro-4-(cyclopropylethynyl)-4-(trifluoromethyl)-1,4-dihydro-2H-benzo[d][1,3]oxazin-2-one;
(S)-7-((2-aminopyrimidin-4-yl)methyl)-4-(cyclopropylethynyl)-4-(1,1-difluoroethyl)-6-fluoro-1,4-dihydro-2H-benzo[d][1,3]oxazin-2-one; and
(S)-7-((2-aminopyrimidin-4-yl)methyl)-6-chloro-4-(cyclopropylethynyl)-4-(1,1-difluoroethyl)-1,4-dihydro-2H-benzo[d][1,3]oxazin-2-one;

or a pharmaceutically acceptable salt thereof.

9. A pharmaceutical composition comprising an effective amount of the compound of claim 1, or a pharmaceutically acceptable salt thereof, and a pharmaceutically acceptable carrier.

10. The pharmaceutical composition of claim 9 further comprising an effective amount of one or more additional nucleoside or nucleotide HIV reverse transcriptase inhibitors, nucleoside or nucleotide reverse transcriptase translocation inhibitors, non-nucleoside HIV reverse transcriptase inhibitors, HIV integrase inhibitors, HIV fusion inhibitors, HIV entry inhibitors, HIV maturation inhibitors, post-attachment inhibitors and latency reversing agents.

* * * * *